United States Patent
O'Bryant

(10) Patent No.: US 12,287,324 B2
(45) Date of Patent: Apr. 29, 2025

(54) COMPANION DIAGNOSTICS FOR NSAIDS AND DONEPEZIL FOR TREATING SPECIFIC SUBPOPULATIONS OF PATIENTS SUFFERING FROM ALZHEIMER'S DISEASE

(71) Applicant: University of North Texas Health Science Center at Fort Worth, Fort Worth, TX (US)

(72) Inventor: Sid E. O'Bryant, Aledo, TX (US)

(73) Assignee: University of North Texas Health Science Center At Fort Worth, Fort Worth, TX (US)

( * ) Notice: Subject to any disclaimer, the term of this patent is extended or adjusted under 35 U.S.C. 154(b) by 852 days.

(21) Appl. No.: 16/962,917

(22) PCT Filed: Jan. 14, 2019

(86) PCT No.: PCT/US2019/013498
§ 371 (c)(1),
(2) Date: Jul. 17, 2020

(87) PCT Pub. No.: WO2019/143562
PCT Pub. Date: Jul. 25, 2019

(65) Prior Publication Data
US 2022/0107305 A1    Apr. 7, 2022

Related U.S. Application Data

(60) Provisional application No. 62/618,857, filed on Jan. 18, 2018.

(51) Int. Cl.
G01N 33/50 (2006.01)
G01N 33/68 (2006.01)

(52) U.S. Cl.
CPC ..... G01N 33/5008 (2013.01); G01N 33/6869 (2013.01)

(58) Field of Classification Search
CPC .......... G01N 33/5008; G01N 33/6869; G01N 2800/2821
See application file for complete search history.

(56) References Cited

U.S. PATENT DOCUMENTS

| 5,192,753 | A | 3/1993 | McGeer et al. |
| 6,819,956 | B2 | 11/2004 | DiLorenzo |
| 7,598,049 | B2 | 10/2009 | Ray et al. |
| 8,008,025 | B2 | 8/2011 | Zhang |
| 8,430,816 | B2 | 4/2013 | Avinash et al. |
| 11,525,834 | B2 | 12/2022 | O'Bryant |
| 2005/0244890 | A1* | 11/2005 | Davies ............... G01N 33/6851 435/7.1 |
| 2006/0094064 | A1 | 5/2006 | Ray et al. |
| 2008/0220449 | A1* | 9/2008 | Vasan .................... C07K 16/18 435/7.9 |
| 2009/0075395 | A1 | 3/2009 | Lee et al. |
| 2010/0124756 | A1 | 5/2010 | Ray |
| 2010/0233818 | A1 | 9/2010 | Sekiyama |
| 2010/0280562 | A1 | 11/2010 | Pi et al. |
| 2011/0082187 | A1 | 4/2011 | Campbell et al. |
| 2011/0159527 | A1 | 6/2011 | Schlossmacher et al. |
| 2011/0202284 | A1* | 8/2011 | McReynolds .......... G16B 40/20 702/19 |
| 2012/0238835 | A1 | 9/2012 | Hyde et al. |
| 2012/0238837 | A1 | 9/2012 | Hyde et al. |
| 2012/0295281 | A1 | 11/2012 | Rai et al. |
| 2013/0012403 | A1 | 1/2013 | Hu |
| 2014/0018446 | A1 | 1/2014 | Royall et al. |
| 2014/0147863 | A1 | 5/2014 | O'Bryant et al. |
| 2014/0220568 | A1 | 8/2014 | Inze et al. |
| 2014/0315736 | A1 | 10/2014 | Nagele |
| 2015/0086616 | A1* | 3/2015 | Lehrer ................. A61K 9/1694 514/567 |
| 2015/0241454 | A1 | 8/2015 | Sandip et al. |
| 2016/0154010 | A1* | 6/2016 | O'Bryant ............... G16B 20/00 600/300 |

(Continued)

FOREIGN PATENT DOCUMENTS

| WO | 9840061 A1 | 9/1998 |
| WO | 2006020269 A2 | 2/2006 |

(Continued)

OTHER PUBLICATIONS

Parsons Neurotox 2013 24:358-369 (Year: 2013).*
Yiannopoulou J. Central Nervous System Disease Dec. 2020:1-12 (Year: 2020).*
Wei J. Neurology 2018 265: 1844-1849 (Year: 2018).*
2013.*
2018.*
2020.*
Mayeux J. American Soc. Experimental Neuro Therapeutics 2004 vol. 1: 182-188 (Year: 2004).*
Kavanaugh Future Rheumatol. Mar. 2008: 303-305 (Year: 2008).*
Strimbu Curr Opin HIV AIDS May 2010: 463-466 (Year: 2010).*
2004 (Year: 2004).*
2010 (Year: 2010).*

(Continued)

*Primary Examiner* — Changhwa J Cheu
(74) *Attorney, Agent, or Firm* — SAUL EWING LLP; Kathryn Doyle; Domingos J. Silva

(57) ABSTRACT

The present invention includes a method for identifying a patient response to treatment for Alzheimer's Disease with a non-steroidal anti-inflammatory drug (NSAID) or an acetylcholinesterase (AChE) inhibitor drug comprising: obtaining a blood or serum sample from the patient; determining the presence of a proinflammatory endophenotype in the blood or serum sample of the patient; using the proinflammatory endophenotype to detect treatment response (a responder, a stable, a non-responder or an adverse responder); and treating the patient with the NSAID or the AChE inhibitor if the patient is in the responder or the stable treatment response phenotype group; or preventing a treatment with the NSAID or the AChE inhibitor if the patient is a non-responder or an adverse responder.

8 Claims, 1 Drawing Sheet

(56) References Cited

U.S. PATENT DOCUMENTS

| | | |
|---|---|---|
| 2016/0291036 A1 | 10/2016 | O'Bryant et al. |
| 2017/0356903 A1 | 12/2017 | Domenyuk et al. |
| 2019/0219599 A1 | 7/2019 | OBryant et al. |
| 2019/0234967 A1 | 8/2019 | O'Bryant |

FOREIGN PATENT DOCUMENTS

| | | |
|---|---|---|
| WO | 2007094472 A1 | 8/2007 |
| WO | 2007144194 A1 | 12/2007 |
| WO | 2010118035 A2 | 10/2010 |
| WO | 2011143597 A1 | 11/2011 |
| WO | 2014066318 A1 | 5/2014 |
| WO | 2015006489 A1 | 1/2015 |
| WO | 2015081166 A1 | 6/2015 |
| WO | 2017223291 A1 | 12/2017 |
| WO | 2019143562 A1 | 7/2019 |

OTHER PUBLICATIONS

Adapt Research Group , et al., "Naproxen and celecoxib do not prevent AD in early results from a randomized controlled trial", Neurology, vol. 68, 2007, pp. 1800-1808.

Aisen , et al., "Effects of Rofecoxib or Naproxen vs Placebo on Alzheimer disease progression: a randomized controlled trial", JAMA, vol. 289, No. 21, Jun. 4, 2003, pp. 2819-2826.

Aisen , et al., "Neither Rofecoxib Nor Naproxen Slows Cognitive Decline In People With Mild-To-Moderate Alzheimer's Disease", Evidence-Based Healthcare, vol. 7, 2003, pp. 200-201.

Anthony , et al., "Reduced prevalence of AD in users of NSAIDs and H2 receptor antagonists: the Cache County study", Neurology, vol. 54, 2000, pp. 2066-2071.

Duong , et al., "C-reactive Protein-Like Immunoreactivity In The Neurofibrillary Tangles Of Alzheimer's Disease", Brain Res, vol. 749, 1997, pp. 152-156.

Durrenberger , et al., "Common mechanisms in neurodegeneration and neuroinflammation: a BrainNet Europe gene expression microarray study", J Neural Trans, vol. 122, 2015, pp. 1055-1068.

Gotschall, P.E. , "β-amyloid induction of gelatinase B secretion in cultured microglia: inhibition by dexamethasone and indomethacin", NeuroReport, vol. 7, No. 18, 1996, pp. 3077-3080.

Grundman , et al., "Treatment of Alzheimer's Disease: Rationale and Strategies", Neurologic Clinics, vol. 18, 2000, pp. 807-827.

Hall , et al., "The impact of APOE status on relationship of biomarkers of vascular risk and systemic inflammation to neuropsychiatric symptoms in Alzheimer's disease", J Alzheimer's Dis, vol. 40, 2014, pp. 887-896.

Henchcliffe , et al., "Biomarkers of Parkinson's disease and Dementia with Lewy bodies", Prog Neurobiol, vol. 95, 2011, pp. 601-613.

Hirohata , et al., "Non-steroidal anti-inflammatory drugs have anti-amyloidogenic effects for Alzheimer's β-amyloid fibrils in vitro", Neuropharmacol, vol. 49, 2005, pp. 1088-1099.

Iwamoto , et al., "Demonstration of CRP immunoreactivity in brains of Alzheimer's disease: immunohistochemical study using formic acid pretreatment of tissue sections", Neurosci Lett, vol. 177, 1994, pp. 23-26.

Johnson , et al., "A depressive endophenotype of poorer cognition among cognitively healthy community-dwelling adults: Results from the Western Australia Memory Study", Intl J Geriatr Psychiatry, vol. 30, No. 8, 2015, pp. 881-886.

Klegeris , et al., "Non-steroidal anti-inflammatory drugs (NSAIDs) and other anti-inflammatory agents in the treatment of neurodegenerative disease", Curr Alzheimer Res, vol. 2, 2005, pp. 355-365.

Lyketsos , et al., "Developing new treatments for Alzheimer's disease: The who, what, when, and how of biomarker-guided therapies", Int Psychogeriatr, vol. 20, No. 5, 2008, pp. 871-889.

Mackenzie , et al., "Nonsteroidal anti-inflammatory drugs use and Alzheimer-type pathology in aging", Neurology, vol. 50, 1998, pp. 986-990.

McGeer , et al., "The importance of inflammatory mechanisms in Alzheimer disease", Exp Gerontol, vol. 33, No. 5, 1998, pp. 371-378.

Netland , et al., "Indomethacin reverses the microglial response to amyloid β-protein", Neurobiol Aging, vol. 19, No. 3, 1998, pp. 201-2014.

O'Bryant , et al., "Biomarkers of Alzheimer's Disease Among Mexican Americans", J Alzheimer's Dis, vol. 34, No. 4, 2013, pp. 841-849.

Pasinetti , et al., "Clycooxygenase-2 expression is increased in frontal cortex of Alzheimer's disease brain", Neuroscience, vol. 87, No. 2, 1998, pp. 319-324.

Rogers , et al., "Clinical trial of indomethacin in Alzheimer's disease", Neurology, vol. 43, 1993, pp. 1609-1611.

Schmidt , et al., "Early inflammation and dementia: a 25-year follow-up of the Honolulu-Asia Aging Study", Ann Neurol, vol. 52, 2002, pp. 168-174.

Tocco , et al., "Maturational regulation and regional induction of cyclooxygenase-2 in rat brain: implications for Alzheimer's disease", Exp Neurol, vol. 144, 1997, pp. 339-349.

Association As. 2013 "Alzheimer's Disease facts and figures" Alzheimers Dement. 2013;9:1-72.

Bas A In't Veld, et al. "Nonsteroidal antiinflammatory drugs and the risk of Alzheimer's disease" N Engl J Med. 2001;345:1515-1521.

Breitner, et al. "Extended results of the Alzheimer's disease antiinflammatory prevention trial" Alzheimers Dement. 2011;7:402-411.

Cunningham, et al. "Oxidative stress, testosterone, and cognition among caucasian and mexican-american men with and without Alzheimer's disease" J Alzheimers Dis. 2014;40:563-573.

Etminan, et al. "Effect of non-steroidal anti-inflammatory drugs on risk of Alzheimer's disease: Systematic review and meta-analysis of observational studies" BMJ. 2003;327:128.

Gasparini, et al. "Non-steroidal anti-inflammatory drugs (NSAIDs) in Alzheimer's disease: Old and new mechanisms of action" J Neurochem. 2004;91:521-536.

Heneka, et al. "Innate immune activation in neurodegenerative disease" Nat Rev Immunol. 2014;14:463-477.

Hurd, et al. "Monetary costs of dementia in the United States" N Engl J Med. 2013;368:1326-1334.

Johnson, et al. "A Depressive Endophenotype of Mild Cognitive Impairment and Alzheimer's Disease" PLoS One. 2013;8:e68848.

Korean Intellectual Property Office (ISA/KR) International Search Report and Written Opinion for PCT/US2019/013498, dated Apr. 29, 2019, 12 pp.

O'Bryant, et al. "A blood based algorithm for the detection of Alzheimer's disease" Dement Geriatr Cogn Disord. 2011;32:55-62.

O'Bryant, et al. A blood-based screening tool for Alzheimer's disease that spans serum and plasma: Findings from TARC and ADNI. PLoS One. 2011;6:e28092.

O'Bryant, et al. "Decreased C-reactive protein levels in alzheimer disease" J Geriatr Psychiatry Neurol. 2010;23:49-53.

O'Bryant, et al. "Risk factors for mild cognitive impairment among Mexican Americans" Alzheimers Dement. 2013;9:622-631.

O'Bryant, et al. "Texas Alzheimer's Research Consortium. A serum protein-based algorithm for the detection of Alzheimer disease" Arch Neurol. 2010;67:1077-1081.

O'Bryant, et al. "Texas Research and Care Consortium. The link between c-reactive protein and Alzheimer's disease among Mexican Americans" J Alzheimers Dis. 2013;34:701-706.

O'Bryant, et al. A proinflammatory endophenotype predicts treatment response in a multicenter trial of NSAIDs in AD, Alzheimer's & dementia: the journal of the Alzheimer's Association, 2014, vol. 10, No. 4, supplement, pp. p. 273-p. 274, See p. 273-p. 274.

O'Bryant, et al., "A serum protein-based algorithm for the detection of Alzheimer disease", Arch. Neurol., 2010, vol. 67, No. 9, pp. 1077-1081, See the whole document.

Hu, et al. "Biomarker discovery for Alzheimer's disease, frontotemporal lobar degeneration, and Parkinson's disease" Acta Neuropathol. 2010;120:385-399.

Thal, et al. "Rofecoxib Protocol 078 study group. A randomized, double-blind, study of rofecoxib in patients with mild cognitive impairment" Neuropsychopharmacology. 2005;30:1204-1215.

(56) References Cited

OTHER PUBLICATIONS

McKeith, et al., "Diagnosis and management of dementia with Lewy bodies: Fourth consensus report of the DLB Consortium", Neurology, 89(1), 2017, pp. 88-100.

McKeith, et al., "Operational criteria for senile dementia of Lewy body type (SDLT)", Psychological medicine, 22(4), 1992, pp. 911-922.

McKeith, et al., "Sensitivity and specificity of dopamine transporter imaging with 123I-FP-CIT SPECT in dementia with Lewy bodies: a phase III, multicentre study", Lancet Neurology, 6(4), 2007, pp. 305-313.

McKeith, et al., "The clinical diagnosis and misdiagnosis of senile dementia of Lewy body type (SDLT)", British Journal of Psychiatry, 165, 1994, pp. 324-332.

McKhann, et al., "Clinical diagnosis of Alzheimer's disease: Report of the NINCDS-ADRDA Work Group under the auspices of Department of Health and Human Services Task Force on Alzheimer's Disease", Neurology, vol. 34, 1984, pp. 939-944.

Mollenhauer, et al., "Serum heart-type fatty acid-binding protein and cerebrospinal fluid tau: marker candidates for dementia with Lewy bodies", Neurodegener Dis, 4(5), 2007, pp. 366-375.

Mueller, et al., "Ways toward an early diagnosis in Alzheimer's disease: The Alzheimer's Disease Neuroimaging Initiative (ADNI)", Alzheimer's and Dementia, vol. 1(1), 2005, pp. 55-66.

Murray, et al., "MRI and pathology of REM sleep behavior disorder in dementia with Lewy bodies", Neurology, 81(19), 2013, pp. 1681-1689.

Nakamura, et al., "High performance plasma amyloid-beta biomarkers for Alzheimer's disease", Nature, vol. 554, 2018, pp. 249-254.

Nilufer, E-T, "Gene expression endophenotypes: a novel approach for gene discovery in Alzheimer's disease", Molecular Neurodegeneration, 6(31), 2011, pp. 1-18.

Novak, et al., "Hispanics/Latinos and Alzheimer's Disease", Alzheimer's Association, May 18, 2004, pp. 1-8.

O'Bryant, et al., "A blood screening test for Alzheimer's disease", Alzheimer's & Dementia: Diagnosis, Assessment & Disease Monitoring, vol. 3, Jun. 25, 2016, pp. 83-90.

O'Bryant, et al., "Biomarkers of Alzheimer's Disease Among Mexican Americans", J Alzheimers Dis,, Dec. 2007, pp. 1-9.

O'Bryant, et al., "Brain-Derived Neurotrophic Factor Levels in Alzheimer's Disease", J Alzheimers Dis, 17(2), 2009, pp. 337-341.

O'Bryant, et al., "Characterization of Mexican Americans with Mild Cognitive Impairment and Alzheimer's Disease", Journal of Alzheimer's Disease, vol. 33, 2012, pp. 373-379.

O'Bryant, et al., "Comparing biological markers of Alzheimer's disease across blood fraction and platforms: Comparing apples to oranges", Alzheimer's & Dementia: Diagnosis, Assessment & Disease Monitoring, vol. 3, 2016, pp. 27-34.

O'Bryant, et al., "Discrepancies between self-reported years of education and estimated reading level among elderly community-dwelling African-Americans: Analysis of the MOAANS data", Arch Clin Neuropsychol, vol. 22, 2007, pp. 327-332.

O'Bryant, et al., "Estimating the Predictive Value of the Test of Memory Malingering: An Illustrative Example for Clinicians", Clin Neuropsychol, 20(3), 2006, pp. 533-540.

O'Bryant, et al., "Guidelines for the Standarization of Preanalytic Variables for Blood-Based Biomarker Studies in Alzheimer's Disease Research", Alzheimer's & Dementia, 2014, pp. 1-12.

O'Bryant, et al., "Molecular Neuropsychology: Creation of Test-Specific Blood Biomarker Algorithms", Dement Geriatr Cogn Disord, vol. 37, 2014, pp. 45-57.

O'Bryant, et al., "Serum Brain-Derived Neurotrophic Factor Levels Are Specifically Associated with Memory Performance among Alzheimer's Disease Cases", Dement Geriatr Cogn Disord, vol. 31, 2011, pp. 31-36.

O'Bryant, et al., "Validation of a Serum Screen for Alzheimer's Disease Across Assay Platforms, Species, and Tissues", J Alzheimers Dis, vol. 42, No. 4, Jan. 1, 2014, pp. 1325-1335.

Oh, et al., "Comparison of Conventional ELISA with Electrochemiluminescence Technology for Detection of Amyloid-B in Plasma", J Alzheimers Dis, 21(3), 2010, pp. 769-773.

Okereke, et al., "A profile of impaired insulin degradation in relation to late-life cognitive decline: A preliminary investigation", Int J Geriatr Psychiatry, 24(2), 2009, pp. 177-182.

Park, et al., "Differential Diagnosis of Patients with Inconclusive Parkinsonian Features Using [18F]FP-CIT PET/CT", Nuclear Medicine and Molecular Imaging, 48(2), published online Dec. 11, 2013, 2014, pp. 106-113.

Petersen, R.C., "Mild Cognitive Impairment Clinical Trials", Nature, vol. 2, Aug. 2003, pp. 646-653.

Petersen, et al., "Mild Cognitive Impairment: An Overview", CNS Spectrums, 13(1), 2008, pp. 45-53.

Piazza, et al., "Increased tissue factor pathway inhibitor and homocysteine in Alzheimer's disease", Neurobiology of Aging, vol. 33, 2010, pp. 226-233.

Piper, et al., "Diagnostic and Predictive Accuracy of Blood Pressure Screening Methods with Consideration of Rescreening Intervals: A Systematic Review for the U.S. Preventive Services Task Force", Ann Internal Med, 162(3), 2015, pp. 192-204.

Plumb, et al., "Sensitivity and specificity of CT colonography for the detection of colonic neoplasia after positive faecal occult blood testing: Systematic review and meta-analysis", Eur Radiol, 24(5), 2014, pp. 1049-1058.

Postuma, et al., "MDS clinical diagnostic criteria for Parkinson's disease", Mov Disord, 30(12), 2015, pp. 1591-1601.

Pykkö, et al., "APOE4 predicts amyloid-β in cortical brain biopsy but not idiopathic normal pressure hydrocephalus", Journal of Neurology, Neurosurgery and Psychiatry, 83(11), 2012, pp. 1119-1124.

Reddy, et al., "dentification of Candidate IgG Biomarkers for Alzheimer's Disease via Combinatorial Library Screening", Cell, vol. 144, 2011, pp. 132-142.

Richartz, et al., "Decline of Immune Responsiveness: A Pathogenetic Factor in Alzheimer's Disease?", J Psychiatric Res, vol. 39, 2005, pp. 535-543.

Scherzer, et al., "GATA transcription factors directly regulate the Parkinson's disease-linked gene alpha-synuclein", Proc Natl Acad Sci USA, 105(31), 2008, pp. 10907-10912.

Scherzer, et al., "Molecular markers of early Parkinson's disease based on gene expression in blood", Proc Natl Acad Sci USA, 104(3), 2007, pp. 955-960.

Schneider, et al., "Biological marker candidates of alzheimer's disease in blood, plasma, and serum", CNS Neuroscience and Therapeutics, 15(4), 2009, pp. 358-374.

Shaw, et al., "Biomarkers of neurodegeneration for diagnosis and monitoring therapeutics", Nature Reviews. Drug Discovery, 6(4), 2007, pp. 295-303.

Shtilbans, et al., "Biomarkers in Parkinson's disease: An update", Current Opinion in Neurology, 2(4), 2012, pp. 460-465.

Sinha, et al., "Biomarkers in dementia with Lewy bodies: A review", International Journal of Geriatric Psychiatry, 27(5), 2012, pp. 443-453.

Sudduth, et al., "Neuroinflammatory phenotype in early Alzheimer's disease", Neurobiol Aging, 34(4), 2013, pp. 1051-1059.

Sverzellati, et al., "Low-dose computed tomography for lung cancer screening: comparison of performance between annual and biennial screen", Eur Radiol, vol. 26, 2016, pp. 3821-3829.

Swardfager, et al., "A Meta-Analysis of Cytokines in Alzheimer's Disease", Biol Psychiatry, vol. 68, 2010, pp. 930-941.

Szerlip, et al., "Association of cognitive impairment with chronic kidney disease in Mexican Americans", J Am Geriatric Soc, 63(10), 2015, pp. 2023-2028.

Thaker, G., "Schizophrenia Endophenotypes as Treatment Targets", Expert Opin Ther Targets, vol. 11, No. 9), 2007, pp. 1189-1206.

Thal, et al., "The Role of Biomarkers in Clinical Trials for Alzheimer Disease", Alzheimer Dis Assoc Disord, 20(1), 2006, pp. 6-15.

Van Blitterswijk, et al., "Anti-superoxide dismutase antibodies are associated with survival in patients with sporadic amyotrophic lateral sclerosis", Amyotroph Lateral Scler, 12(6), 2011, pp. 430-438.

(56) References Cited

OTHER PUBLICATIONS

Van Den Dungen, et al., "The accuracy of family physicians' dementia diagnoses at different stages of dementia: A systematic review", International Journal of Geriatric Psychiatry, 27(4), 2012, pp. 342-354.
Van Oijen, et al., "Plasma Abeta(1-40) and Abeta(1-42) and the risk of dementia: a prospective case-cohort study", Lancet Neurology, 5(8), 2006, pp. 655-660.
Villareal, et al., "Serum-based protein profiles of Alzheimer's disease and mild cognitive impairment in elderly Hispanics", Neurodegener Dis Manag, vol. 6, No. 3, 2016, pp. 203-213.
International Search Report and Written Opinion issued in App. No. PCT/US2022/018974, mailing date Jun. 2, 2022, 21 pages.
Lista (Progress in Neurobiology 101-102 (2013) pp. 1-17 Pub online Jun. 26, 2012).
Prasad (Cardiovascular Drug Reviews vol. 24 No. 1 pp. 33-50 2006).
Pujos (Anal Bioanal Chem 2005 381:244-254).
Vignini et al., "Alzheimer's Disease and Diabetes: New Insights and Unifying Therapies", Current Diabetes Reviews, Sep. 2013, 000-000.
Akiyama, et al., "Inflammation and Alzheimer's disease", Neurobiol Aging, 21(3), 2000, pp. 383-421.
Al-Jarrah, et al., "Treadmill exercise training could attenuate the upregulation of Interleukin-1beta and tumor necrosis factor alpha in the skeletal muscle of mouse model of chronic/progressive Parkinson disease", Neuro Rehabilitation, 43, 2018, pp. 501-507.
Alves, et al., "CSF amyloid-β and tau proteins, and cognitive performance, in early and untreated Parkinson's Disease: The Norwegian ParkWest study", Journal of Neurology, Neurosurgery and Psychiatry, 81(10), 2010, pp. 1080-1086.
American Gerontological Society, "The Gerontological Society of American Workgroup on Cognitive Impairment Detection: Report and Recommendations", 2015.
Anonymous, "Clinical and neuropathological criteria for frontotemporal dementia", J Neurol Neurosurg and Psychiatry, vol. 57, 1994, pp. 416-418.
Anonymous, "Consensus report of the Working Group on: "Molecular and Biochemical Markers of Alzheimer's Disease"", Neurobiology of Aging, vol. 19, No. 2, 1998, pp. 109-116.
Arora, et al., "Diagnostic accuracy of point-of-care testing for diabetic ketoacidosis at emergency-department triage: 3-hydroxybutyrate versus the urine dipstick", Diabetes Care, 34(4), 2011, pp. 852-854.
Bandason, et al., "Validation of a screening tool to identify older children living with HIV in primary care facilities in high HIV prevalence settings", AIDS, 30(5), 2016, pp. 779-7895.
Barber, et al., "An Inflammatory Endophenotype of Alzheimer's Disease", Poster Presentations P3-267, Alzheimer's and Dementia, 6(f) Supplement: S530, 2010, 1 pg.
Barker, et al., "Relative frequencies of Alzheimer disease, Lewy body, vascular and frontotemporal dementia, and hippocampal sclerosis in the State of Florida Brain Bank", Alzheimer Dis Assoc Disord, 16(4), 2002, pp. 203-212.
Bauer, et al., "Examining the test of memory malingering trial 1 and word memory test immediate recognition as screening tools for insufficient effort", Assessment, 14(3), 2007, pp. 215-222.
Belmin, et al., "Assessment and Management of Patients with Cognitive Impairment and Dementia in Primary Care", J Nutr, Health Aging, vol. 16, 2012, pp. 462-467.
Benadiba, et al., "New Molecular Targets for PET and SPECT Imaging in Neurodegenerative Diseases", Rev Bras Psiquiatr, 34(Suppl 2), 2012, pp. S125-S148.
Bhavadharini, et al., "Use of capillary blood glucose for screening for gestational diabetes mellitus in resource-constrained settings", Acta Diabetologica, vol. 53(1), 2016, pp. 91-97.
Biomarkers Definitions Working G, "Biomarkers and surrogate endpoints: Preferred definitions and conceptual framework", Clin Pharmacol Ther, 69(3), 2001, pp. 89-95.

Birrer, et al., "Depression in later life: A diagnostic and therapeutic challenge", American Family Physician, 69(10), 2004, pp. 2375-2382.
Bjerke, "Confounding Factors Influencing Amyloid Beta Concentration in Cerebrospinal Fluid", Int J Alzheimers Dis, vol. 2010, Art. 986310, 2010, pp. 1-11.
Blasko, I., "Ibuprofen decreases cytokine-induced amyloid beta production in neuronal cells", Neurobiology of Disease, 8(6), 2001, pp. 1094-1101.
Bond, et al., "Screening for cognitive impairment, Alzheimer's disease and other dementias: Opinions of European caregivers, payors, physicians and the general public", Journal of Nutrition, Health and Aging, 14(7), 2010, pp. 558-562.
Braskie, et al., "Neuroimaging measures as endophenotypes in Alzheimer's disease", Int J Alzheimer's Dis, vol. 2011, Art. 490140, 2011, 16 pages.
Breiman, "Random Forests", Machine Learning, vol. 45, Issue 1, Oct. 2001, pp. 5-32.
Britschgi, et al., "Blood protein signature for early diagnosis of Alzheimer disease", Archives of Neurology, vol. 66, No. 2, Feb. 2009, pp. 161-165.
Brothers, et al., "Are inflammatory profiles the key to personalized Alzheimer's treatment?", Neurodegenerative Disease Management vol. 3, 2013, pp. 343-351.
Campari, et al., "Impact of the Introduction of Digital Mammography in an Organized Screening Program on the Recall and Detection Rate", J Digital Imaging, vol. 29(2), 2016, pp. 235-242.
Chan, E, "Expression Analyses and molecular biological studies contribute to a systems-level understanding of host response, and new analytical software tools can help", G&P Magazine 6(3), 2006, pp. 20-26.
Chatterjee, et al., "Comparative analysis of RNA-Seq data from brain and blood samples of Parkinson's disease", Biochem Biophys Res Commun, vol. 484, 2017, pp. 557-564.
Cho, et al., "Selective translational control of the Alzheimer amyloid precursor protein transcript by iron regulatory protein-1", J Biol Chem, 285(41), 2010, pp. 31217-31232.
Clark, et al., "Advances in blood-based protein biomarkers for Alzheimer's disease", Alzheimer's Research and Therapy, vol. 5, No. 3, May 9, 2013, pp. 18.
Clark, et al., "Diagnostic accuracy of Percent retention scores on RBANS verbal memory subtests for the diagnosis of Alzheimer's disease and mild cognitive impairment", Archives of Clinical Neuropsychology, 25(4), 2010, pp. 318-326.
Colangelo, et al., "Gene Expression Profiling of 12633 Genes in Alzheimer Hippocampal CA1: Transcription and Neurotrophic Factor Down-Regulation and Up-Regulation of Apoptotic and Pro-Inflammatory Signaling", Journal of Neuroscience Research, vol. 70, May 10, 2002, pp. 462-473.
Coleman, Robert A., "Of mouse and man—what is the value of the mouse in predicting gene expression in humans?", Drug Discovery Today, 8(6), Mar. 2003, 233-235.
Colloby, et al., "A comparison of 99mTc-exametazime and 123I-FP-CIT SPECT imaging in the differential diagnosis of Alzheimer's disease and dementia with Lewy bodies", International Psychogeriatrics 20(6), 2008, pp. 1124-1140.
Connell, et al., "Black and white adult family members' attitudes toward a dementia diagnosis", J Amer Geriatrics Soc, vol. 57(9), Sep. 2009, pp. 1562-1568.
Cruchaga, et al., "Cerebrospinal fluid APOE levels: an endophenotype for genetic studies for Alzheimer's disease", Human Molecular Genetics, 2012, pp. 1-14.
Cummings, et al., "Fit-for-purpose biomarker method validation for application in clinical trials of anticancer drugs", British J Cancer, published online Oct. 5, 2010, vol. 103(9), 2010, pp. 1313-1317.
Dickstein, et al., "Role of Vascular Risk Factors and Vascular Dysfunction in Alzheimer's Disease", Mt. Sinai J Med, 77(1), 2010, pp. 82-102.
Ding, et al., "Association of SNCA with Parkinson: replication in the Harvard NeuroDiscovery Center Biomarker Study", Mov Disord, 26(12), 2011, pp. 2283-2286.

(56) References Cited

OTHER PUBLICATIONS

Doecke, et al., "Blood-Based Protein Biomarkers for Diagnosis of Alzheimer Disease", Arch Neurol, vol. 69, No. 10, Oct. 1, 2012, pp. 1318-1325.
Duff, et al., "Diagnostic Accuracy of the RBANS in Mild Cognitive Impairment: Limitations on Assessing Milder Impairments", Arch Clin Neuropsychol, vol. 25, 2010, pp. 429-441.
Duff, et al., "Utility of the RBANS in Detecting Cognitive Impairment Associated with Alzheimer's Disease Sensitivity, Specificity, and Positive and Negative Predictive Powers", Arch Clin Neuropsychol, vol. 23, 2008, pp. 603-612.
During, et al., "The concept of FDG-PET endophenotype in Alzheimer's disease", Neurol Sci, vol. 32, 2011, pp. 559-569.
Edwards, et al., "Combining Select Neuropsychological Assessment with Blood-Based Biomarkers to Detect Mild Alzheimer's Disease: A Molecular Neuropsychology Approach", J Alzheimer's Dis, vol. 42, 2014, pp. 635-640.
Edwards, et al., "Molecular markers of amnestic mild cognitive impairment among Mexican Americans", J Alzheimer's Dis, 49(1), 2016, pp. 221-228.
Edwards, et al., "Molecular markers of neuropsychological functioning and Alzheimer's disease", Alzheimer's & Dementia: Diagnosis, Assessment & Disease Monitoring, vol. 1, No. 1, Mar. 1, 2015, pp. 61-66.
Eller, et al., "α-Synuclein in Parkinson disease and other neurodegenerative disorders", Clinical Chemistry and Laboratory Medicine, 49(3), 2011, pp. 403-408.
Elsafi, et al., "The sensitivity, specificity, predictive values, and likelihood ratios of fecal occult blood test for the detection of colorectal cancer in hospital settings", Clinical and Experimental Gastroenterology, vol. 8, 2015, pp. 279-284.
Emre, et al., "Clinical Diagnostic Driteria for Dementia Associated with Parkinson's Disease", Movement Disorders, 22(12), 2007, pp. 1689-1707.
Fan, et al., "Structural and functional biomarkers of prodromal Alzheimer's disease: a high-dimensional pattern classification study", Neuroimage, 41(2), 2008, pp. 227-285.
Ferman, et al., "Inclusion of RBD improves the diagnostic classification of dementia with Lewy bodies", Neurology 77(9), 2011, pp. 875-882.
Ferreti, et al., "Intracellular Aβ-oligomers and early inflammation in a model of Alzheimer's disease", Neurobiology of Aging, 33(7), 2012, pp. 1329-1342.
Villemagne, et al., "Long night's journey into the day: Amyloid-β imaging in Alzheimer's disease", Journal of Alzheimer's Disease, 33 (Supplement 1), 2013, pp. S349-S359.
Waring, et al., "The Texas Alzheimer's Research Consortium longitudinal research cohort: Study design and baseline characteristics", Texas Public Health Journal 60(3), 2008, pp. 9-13.
Watson, et al., "Screening accuracy for late-life depression in primary care: A systematic review", Journal of Family Practice, 52(12), 2003, pp. 956-964.
Whitehead, et al., "Variation in tissue-specific gene expression among natural populations", Genome Biology, vol. 6, Jan. 26, 2005, pp. R13.1 to R13.14.
Wildburger, et al., "Amyloid-beta Plaques in Clinical Alzheimer's Disease Brain Incorporate Stable Isotope Tracer In Vivo and Exhibit Nanoscale Heterogeneity", Front Neurol, vol. 9, No. 169, 2018, pp. 169.
Wright, et al., "Geographic and ethnic variation in Parkinson disease: a population-based study of US Medicare beneficiaries", Neuroepidemiology, 34(3), 2010, pp. 143-151.
Yokono, K., "Alzheimer Disease as a Diabetic Complication", Japanese Journal of Geriatrics, vol. 47, 2010, pp. 385-389.
Trepanier, C.H., et al., "Neuroinflammation in Alzheimer's Disease: Are NSAIDs and Selective COX-2 Inhibitors the Next Line of Therapy?", Journal of Alzheimer's Disease, vol. 21, No. 4, pp. 1089-1099, 2010.

Fillit, et al., "Economics of dementia and pharmacoeconomics of dementia therapy", Am J Geriatric Pharmacotherapy, vol. 3(1), Mar. 2005, pp. 39-49.
Fiss, et al., "Cognitive impairment in primary ambulatory health care: Pharmacotherapy and the use of potentially inappropriate medicine", International Journal of Geriatric Psychiatry, 28(2), 2013, pp. 173-181.
Fujishiro, et al., "Validation of the neuropathologic criteria of the third consortium for dementia with lewy bodies for prospectively diagnosed cases", Journal of Neuropathology and Experimental Neurology, 67(7), 2008, pp. 649-656.
Gerlach, et al., "Biomarker candidates of neurodegeneration in Parkinson's disease for the evaluation of disease-modifying therapeutics", Journal of Neural Transmission, 119(1), 2012, pp. 39-52.
Gold, et al., "The emergence of diagnostic imaging technologies in breast cancer: Discovery, regulatory approval, reimbursement, and adoption in clinical guidelines", Cancer Imaging, 12(1), 2012, pp. 13-24.
Gottesman, et al., "Genetic theorizing and schizophrenia", British Journal of Psychiatry, 122(566), 1973, pp. 15-30.
Gottesman, et al., "The endophenotype concept in psychiatry: etymology and strategic intentions", Am J Psychiatry, 160(4), 2003, pp. 636-645.
Graff-Radford, et al., "Imaging and acetylcholinesterase inhibitor response in dementia with Lewy bodies", Brain, 135(8), 2012, pp. 2470-2477.
Green, et al., "Alterations of p11 in brain tissue and peripheral blood leukocytes in Parkinson's disease", Proc Natl Acad Sci USA, 114(10), 2017, pp. 2735-2740.
Groveman, et al., "Rapid and ultra-sensitive quantitation of disease-associated alpha-synuclein seeds in brain and cerebrospinal fluid by alphaSyn RT-QuIC", Acta Neuropathologica Communications, 6(7), 2018, pp. 1-10.
Hakimi, et al., "Parkinson's disease-linked LRRK2 is expressed in circulating and tissue immune cells and upregulated following recognition of microbial structures", J Neural Transm, 118(5), 2011, pp. 795-808.
Hall, et al., "Biomarkers of Vacular Risk, Systemic Inflammation, and Microvascular Pathology and Neuropsychiatric Symptoms in Alzheimer's Disease", J Alzheimer's Dis, vol. 35, 2013, pp. 363-371.
Halliday, et al., "Neuropathology underlying clinical variability in patients with synucleinopathies", Acta neuropathologica, 122(2), 2011, pp. 187-204.
Hampel, et al., "Precision Medicine: The Golden Gate for detection, treatment and prevention of Alzheimer's disease", J Prev Alzheimer's Dis, 3(4), 2016, pp. 243-259.
Hansson, et al., "Blood-based NfL: A biomarker for differential diagnosis of parkinsonian disorder", Neurology, vol. 88, 2017, pp. 930-937.
Harvey, et al., "A systematic review of the diagnostic accuracy of prostate specific antigen", BMC Urology, vol. 9(1), Sep. 10, 2009.
Hely, et al., "The Sydney multicenter study of Parkinson's disease: the inevitability of dementia at 20 years", Mov Disord, 23(6), 2008, pp. 837-844.
Hennecke, et al., "RNA biomarkers of Parkinson's disease: developing tools for novel therapies", Biomark Med, 2(1), 2008, pp. 41-53.
Henriksen, "The future of blood-based biomarkers for Alzheimer's disease", Alzheimers Dement, 10(1), 2014, pp. 115-131.
Higuchi, et al., "Glucose hypometabolism and neuropathological correlates in brains of dementia with Lewy bodies", Exp Neurol, 162(2), 2000, p. 247-256.
Ho, et al., "Bridging molecular genetics and biomarkers in Lewy body and related disorders", Int J Alzheimer's Dis, vol. 2011, Art. 842475, 2011, pp. 1-18.
Hu, et al., "Transcriptional modulator H2A histone family, member Y (H2AFY) marks Huntington disease activity in man and mouse", Proc Natl Acad Sci USA, 108(41), 2011, pp. 17141-17146.
Humpel, C., "Identifying and validating biomarkers for Alzheimer's disease", Trends in Biotechnology, vol. 29, No. 1, Jan. 2011, pp. 26-32.

(56) References Cited

OTHER PUBLICATIONS

Huse, et al., "Burden of illness in Parkinson's disease", Mov Disord, 20(11), 2005, pp. 1449-1454.
Jani, et al., "Recommendations for Use and Fit-for-Purpose Validation of Biomarker Multiplex Ligand Binding Assays in Drug Development", AAPS Journal, vol. 18, No. 1, 2016, pp. 1-14.
Janocko, et al., "Neuropathologically defined subtypes of Alzheimer's disease differ significantly from neurofibrillary tangle-predominant dementia", Acta Neuropathologica, 124(5), 2012, pp. 681-692.
Johnson, "Comorbid Depression and Diabetes as a Risk for Mild Cognitive Impairment and Alzheimer's Disease in Elderly Mexican Americans", J Alzheimer's Dis, vol. 47, 2015, pp. 129-136.
Kaerst, et al., "Using cerebrospinal fluid marker profiles in clinical diagnosis of dementia with lewy bodies, Parkinson's disease, and Alzheimer's disease", J Alzheimers Dis, 38(1), 2014, pp. 63-73.
Kantarci, et al., "Multimodality Imaging Characteristics of Dementia with Lewy bodies", Neurobiol Aging, 33(9), 2012, pp. 2091-2105.
Kim, "Interactions between pro-inflammatory cytokines and statins on depression in patients with acute coronary syndrome", Prog Neuropsychopharmacol Biol Psychiatry, 80, Pt C, 2018, pp. 250-254.
Knopman, et al., "Patterns of Care in the Early Stages of Alzheimer's Disease: Impediments to Timely Diagnosis", J Am Geriatrics Soc, vol. 48(3), 2000, pp. 300-304.
Kosaka, "Presenile dementia with Alzheimer-, Pick- and Lewy-body changes", Acta neuropathologica, vol. 36, No. 3, 1976, pp. 221-233.
Kounnas, "Modulation of g-Secretase Reduces b-Amyloid Deposition in a Transgenic Mouse Model of Alzheimer's Disease", Neuron, vol. 67, 2010, pp. 769-780.
Koyama, et al., "The Role of Peripheral Inflammatory Markers in Dementia and Alzheimer's Disease: A Meta-Analysis", J Geronol A Biol Sci Med Sci, vol. 68, No. 4, Apr. 2013, pp. 433-440.
Kuhle, et al., "A highly sensitive electrochemiluminescence immunoassay for the neurofilament heavy chain protein", J Neuroimmunol, vol. 220, Nos. 1-2, 2010, pp. 114-119.
Landers, et al., "A High-Intensity Exercise Boot Camp for Persons with Parkinson Disease: A Phase II, Pragmatic, Randomized Clinical Trial of Feasibility, Safety, Signal of Efficacy, and Disease Mechanisms", J Neurol Phys Ther, vol. 43, No. 1, 2019, pp. 12-25.
Laske, et al., "Identification of a blood-based biomarker panel for classification of Alzheimer's disease", Int J Neuropsychopharmacol, vol. 14, 2011, pp. 1147-1155.
Laske, et al., "Immune Profiling in Blood Identifies sTNF-R1 Performing Comparably Well as Biomarker Panels for Classification of Alzheimer's Disease Patients", J Alzheimer's Dis, 34(2), 2013, pp. 367-375.
Lee, et al., "Fit-for-purpose Method Development and Validation for Successful Biomarker Measurement", Pharmaceutical Res, vol. 23(2), 2006, pp. 312-328.
Lee, et al., "The National Mammography Database: Preliminary Data", Am J Roentgenology, 206(4), 2016, pp. 883-890.
Leung, et al., "Inflammatory Proteins in Plasma Are Associated with Severity of Alzheimer's Disease", PLoS One, vol. 8, Issue 6, Jun. 2013, pp. e64971 (1-10).
Liu, et al., "Prediction of cognition in Parkinson's disease with a clinical-genetic score: a longitudinal analysis of nine cohorts", Lancet Neurol, 16(8), 2017, pp. 620-629.
Liu, et al., "Specifically neuropathic Gaucher's mutations accelerate cognitive decline in Parkinson's", Ann Neurol, 80(5), 2016, pp. 674-685.
Lo, et al., "Relationship between patient age and duration of physician visit in ambulatory setting: Does one size fit all?", J Am Geriatrics Soc, 53(7), 2005, pp. 1162-1167.
Locasio, et al., "Association between alpha-synuclein blood transcripts and early, neuroimaging-supported Parkinson's disease", Brain, 138 (Pt 9), 2015, pp. 2659-2671.
Lopponen, et al., "Diagnosing cognitive impairment and dementia in primary health care—a more active approach is needed", Age and Ageing, 32(6), 2003, pp. 606-612.
Lundquist, et al., "Screening for Alzheimer's Disease: Inspiration and Ideas from Breast Cancer Strategies", J Appl Gerontol, 34(3), 2015, pp. 317-328.
Maeck, et al., "Dementia diagnostics in primary care: a representative 8-year follow-up study in lower Saxony, Germany", Dement Geriatr Cogn Disord, vol. 25, No. 2, 2008, pp. 127-134.
Martin, et al., "Recruitment of Mexican-American Adults for an Intensive Diabetes Intervention Trial", Ethn Dis, 21(1), 2011, pp. 7-12.
McKeith, et al., "An evaluation of the predictive validity and inter-rater reliability of clinical diagnostic criteria for senile dementia of Lewy body type", Neurology, 44(5), 1994, pp. 872-877.

\* cited by examiner

COMPANION DIAGNOSTICS FOR NSAIDS AND DONEPEZIL FOR TREATING SPECIFIC SUBPOPULATIONS OF PATIENTS SUFFERING FROM ALZHEIMER'S DISEASE

CROSS-REFERENCE TO RELATED APPLICATIONS

This application is the National Stage of International Application No. PCT/US2019/013498, filed on Jan. 14, 2019 claiming the priority of 62/618,857 filed on Jan. 18, 2018, the content of each of which is incorporated by reference herein.

STATEMENT OF FEDERALLY FUNDED RESEARCH

This invention was made with government support under AG039389, AG051848 awarded by National Institutes of Health. The government has certain rights in the invention.

TECHNICAL FIELD OF THE INVENTION

The present invention relates in general to the field of determining which Alzheimer's disease patients are responsive or stable from NSAID or acetylcholinesterase (AchE) inhibitor treatment, are not likely to respond to NSAID or AChE inhibitor treatment, and those for which the NSAID or AChE inhibitor treatment is contra-indicated.

BACKGROUND OF THE INVENTION

Without limiting the scope of the invention, its background is described in connection with Alzheimer's disease.

Currently, over 5 million Americans suffer from Alzheimer's disease (AD; the most common form of neurodegenerative dementia)[1] and it is estimated that those numbers will grow exponentially. AD has an annual health care cost similar to that of cardiovascular disease (CVD) and more than cancer [2]. While death rates due to CVD and cancer have declined in recent decades, death rates due to AD have steadily increased [1] due to a lack of effective disease-modifying therapeutics. AD is a heterogeneous condition and the identification of specific therapeutically relevant subpopulations could significantly enhance therapeutic options [3].

Profiling biological pathways associated with neurodegenerative disease has been posited to highlight novel pathways for therapeutics [4, 5], with inflammation being a major implicated pathway[6, 7]. Numerous studies link inflammation to AD [8, 9]. For example, in the inventor's prior work it was found that inflammation played a key role in a serum-based proteomic profile for the detection of AD [10-12]. Accordingly, a major hypothesis in the field is that anti-inflammatory compounds have the potential for treating AD and other neurodegenerative diseases [13, 16-21]. However, none of several randomized clinical trials using NSAIDs has been successful in treating or preventing AD despite promising early phase clinical trial data [22-24]. Therefore, a need remains for effective treatments that are customized to a particular patient's response to AD. There is also a long-standing clinical awareness that cholinesterase inhibitors help some patients whereas they have no benefit or even a detrimental effect on others. However, to date, predicting these outcomes have been unsuccessful. It is also hypothesized that there is a subgroup of patients that will respond maximally to cholinesterase inhibitors and that inflammatory markers may identify these patients.

SUMMARY OF THE INVENTION

In one embodiment, the present invention includes a method for identifying a patient response to treatment for Alzheimer's Disease with a non-steroidal anti-inflammatory drug (NSAID) comprising: obtaining a blood or serum sample from the patient; determining the presence of a proinflammatory endophenotype in the blood or serum sample of the patient; using the proinflammatory endophenotype to detect a treatment response (a responder, a stable, a non-responder or an adverse responder); and treating the patient with the NSAID if the patient is in the responder or the stable treatment response phenotype group; or preventing a treatment with the NSAID if the patient is a non-responder or an adverse responder. In one aspect, the proinflammatory endophenotypes is determined using CRP and TNFα. In another aspect, the proinflammatory endophenotype is determined using TNFα, CRP, IL6, and IL10 biomarkers. In another aspect, the proinflammatory endophenotype proteins assayed are: TNFα, CRP, IL5, IL6, IL7, IL10 and IL18. In another aspect, the treatment response is selected from a responder, a stable, a non-responder or an adverse responder. In another aspect, the expression level of the proinflammatory endophenotype proteins is determined by detecting the proteins. In another aspect, the expression level of the proinflammatory endophenotype proteins is determined by detecting nucleic acids. In another aspect, the NSAIDS are selected from at least one of: naproxen, rofecoxib, ibuprofen, ketoprofen, tolmetin, diclofenac, fenoprofen, flurbiprofen, piroxicam, etodolac, ketorolac, imdomethacin, nabumetone, oxaprozin, or mefenamic acid. In another aspect, the method further comprises the step of ranking the expression of the proinflammatory endophenotype proteins and correlating them to the NSAID. In another aspect, the method further comprises the step of ranking the expression of the proinflammatory endophenotype proteins in the following order: TNFα, CRP, IL6, and IL10, and correlating them to response to naproxen. In another aspect, the method further comprises the step of ranking the expression of the proinflammatory endophenotype proteins in the following order: TNFα, CRP, IL6, and IL10, and correlating them to response to rofecoxib. In one aspect, the method further comprises determining the expression level of IL5, IL7, and IL18. In another aspect, the method has an accuracy of greater than 93, 94, 95, 96, 97, 98, 99, or 100% predictive value. In another aspect, the method further comprises the step of excluding patients from treatment with NSAIDs. In another aspect, the method further comprises step of stopping NSAID treatment for patients in which NSAIDs are contraindicated.

In another embodiment, the present invention includes a method for dividing Alzheimer's Disease into subgroups that correlate with responsiveness to treatment with a non-steroidal anti-inflammatory (NSAID) drug comprising: obtaining a blood or serum sample from a patient; determining the presence of a proinflammatory endophenotype in the blood or serum sample from an expression of TNFα, CRP, IL6, and IL10; and using the proinflammatory endophenotype to detect a treatment response (a responder, a stable, a non-responder or an adverse responder) for treatment with the NSAID. In one aspect, the expression levels of TNFα, CRP, IL6, and IL10, are determined by detecting proteins and/or nucleic acids. In another aspect, the method further comprises detecting the expression levels of IL5, IL7, and IL18 is determined by detecting proteins and/or nucleic acids. In another aspect, the treatment response is selected from a responder, a stable, a non-responder or an adverse responder. In another aspect, the NSAIDS are selected from at least one of: naproxen, Rofecoxib, ibuprofen, ketoprofen, tolmetin, diclofenac, fenoprofen, flurbiprofen, piroxicam, etodolac, ketorolac, imdomethacin, nabumetone, oxaprozin, or mefenamic acid. In another aspect, the method further comprises the step of ranking the expression of the seven proteins and correlating them to a response to the NSAID. In another aspect, the method further comprises the step of ranking the expression of four or more proteins, and in certain cases seven proteins in the following order: CRP, TNFα, IL5, IL6, IL7, IL18 and IL10 are determined, and correlating them to a response to naproxen. In another aspect, the method further comprises the step of ranking the expression of the seven proteins in the following order: IL10, CRP, IL6, IL18, IL7, TNFα, and IL5, and correlating them to a response to rofecoxib. In another aspect, the treatment response is selected from a responder, a stable, a non-responder or an adverse responder. In another aspect, the method has an accuracy of greater than 93, 94, 95, 96, 97, 98, 99, or 100% predictive value. In another aspect, the method further comprises the step of excluding patients from treatment with NSAIDs. In another aspect, the method further comprises the step of stopping NSAID treatment for patients in which NSAIDs are contraindicated.

In another embodiment, the present invention includes a method for identifying a patient response to treatment for Alzheimer's Disease with an AChE inhibitor drug (e.g., donepezil, Aricept) comprising: obtaining a blood or serum sample from the patient; determining the presence of a proinflammatory endophenotype in the blood or serum sample of the patient; using the proinflammatory endophenotype to detect treatment response (a responder, a stable, a non-responder or an adverse responder); and treating the patient with AChE inhibitor if the patient is in the responder or the stable treatment response phenotype group; or preventing a treatment with AChE inhibitor if the patient is a non-responder or an adverse responder. In one aspect, the proinflammatory endophenotypes is determined using CRP and TNFα. In another aspect, the proinflammatory endophenotype proteins assayed are: TNFα, CRP, IL5, IL6, IL7, IL10 and IL18. In another aspect, the expression level of the proinflammatory endophenotype proteins is determined by detecting the proteins. In another aspect, the expression level of the proinflammatory endophenotype proteins is determined by detecting nucleic acids. In another aspect, the AChE inhibitor is selected from at least one of: donepezil, Aricept, rivastigmine and galantamine. In another aspect, the method further comprises the step of ranking the expression of the proinflammatory endophenotype proteins and correlating them to a response to an AChE inhibitor. In another aspect, the method further comprises the step of ranking the expression of the proinflammatory endophenotype proteins in the following order: IL7, IL18, CRP, IL6, TNFα, IL10 and IL5, and correlating them to response to donepezil. In another aspect, the method has an accuracy of greater than 93, 94, 95, 96, 97, 98, 99, or 100% predictive value. In another aspect, the method further comprises the step of excluding patients from treatment with AChE inhibitor. In another aspect, the method further comprises step of stopping AChE inhibitor treatment for patients in which an AChE inhibitor is contraindicated.

In another embodiment, the present invention includes a method for dividing Alzheimer's Disease into subgroups that correlate with responsiveness to treatment with an AChE inhibitor drug (e.g., donepezil, Aricept) comprising: obtaining a blood or serum sample from a patient; determining the presence of a proinflammatory endophenotype in the blood or serum sample from an expression of TNFα, CRP, IL5, IL6, IL7, IL10, and IL18; and using the proinflammatory endophenotype to detect treatment response (a responder, a stable, a non-responder or an adverse responder) for treatment with the AChE inhibitor. In one aspect, the expression levels of TNFα, CRP, IL5, IL6, IL7, IL10, and IL18 are determined by detecting proteins. In another aspect, the expression levels of TNFα, CRP, IL5, IL6, IL7, IL10, and IL18 are determined by detecting nucleic acids. In another aspect, the AChE inhibitor is selected from at least one of: donepezil, Aricept, rivastigmine and galantamine. In another aspect, the method further comprises the step of ranking the expression of the seven proteins and correlating them to a response to the AChE inhibitor. In another aspect, the method further comprises the step of ranking the expression of the seven proteins in the following order: IL7, IL18, CRP, IL6, TNFα, IL10 and IL5, and correlating them to a response to donepezil. In another aspect, the method has an accuracy of greater than 93, 94, 95, 96, 97, 98, 99, or 100% predictive value. In another aspect, the method further comprises the step of excluding patients from treatment with an AChE inhibitor. In another aspect, the method further comprises the step of stopping AChE inhibitor treatment for patients in which AChE inhibitors are contraindicated.

In another embodiment, the present invention includes a method of analyzing a response of patients previously treated for Alzheimer's Disease with an anti-AD drug comprising: obtaining a database of biomarker expression data from patients treated with an anti-AD drug; determining the presence of a proinflammatory endophenotype in the blood or serum sample with a seven protein algorithm; using the proinflammatory endophenotype to detect treatment response (a responder, stable, non-responder or adverse responder); and determining if an effectiveness of the drug correlates with the patient having the proinflammatory endophenotype. In one aspect, the method has an accuracy of greater than 93, 94, 95, 96, 97, 98, 99, or 100% predictive value. In another aspect, the proinflammatory endophenotype in the blood or serum sample is determined from expression of TNFα, CRP, IL5, IL6, IL7, IL10, and IL18. In another aspect, the database is obtained from a clinical trial.

In another embodiment, the present invention includes a method for excluding patients from recruitment into a clinical study by screening patients for non-responders or adverse responders to NSAID treatment comprising: obtaining a blood or serum sample from a patient; determining the expression levels of TNFα, CRP, IL5, IL6, IL7, IL10, and IL18; determining if the patient has a pro-inflammatory endophenotype; and excluding the patient from recruitment into the clinical study if the patient is ruled out based on a determination that the patient is in a non-responder or adverse responder treatment response phenotype group.

In another embodiment, the present invention includes a method of determining if an NSAID has an effect on Alzheimer's Disease or a neurodegenerative disease, wherein the NSAID has previously failed in a clinical trial or has been shown to have no effect on Alzheimer's Disease or the neurodegenerative disease, comprising: determining a presence of a proinflammatory endophenotype in the blood or serum sample of a patient with Alzheimer's Disease or the neurodegenerative disease; selecting the patient for treatment with the NSAID if the treatment response is a responder or a stable treatment response proinflammatory endophenotype; and determining if the NSAID has an effect on the Alzheimer's Disease or a neurodegenerative disease of the patient. In one aspect, the method further comprises treating the patient with the NSAID, e.g., treating the patient prior to determining the proinflammatory endophenotype. In another aspect, the method further comprises selecting a NSAID that has previously failed in a clinical trial or has been shown to have no statistically significant effect on a population with Alzheimer's Disease or the neurodegenerative disease. In another aspect, the proinflammatory endophenotype is determined using TNFα, CRP, IL6, and IL10 biomarkers. In another aspect, the proinflammatory endophenotype proteins assayed are: TNFα, CRP, IL5, IL6, IL7, IL10 and IL18. In another aspect, the method further comprises the step of excluding patients from treatment with an NSAID if the patient is determined to be in a non-responder or an adverse responder endophenotype group.

In another embodiment, the present invention includes a method for determining an increased likelihood of pharmacological effectiveness of treatment with an NSAID in a patient diagnosed with Alzheimer's Disease comprising: obtaining a blood or serum sample from the patient; determining a presence or absence of a proinflammatory endophenotype in the blood or serum sample of the patient; and using the proinflammatory endophenotype to determine the likelihood of pharmacological effectiveness of the NSAID in the patient, wherein a responder or stable proinflammatory endophenotype indicates an increased likelihood of pharmacological effectiveness of treatment by the NSAID in the patient. In one aspect, the proinflammatory endophenotype is determined from a CRP and a TNFα biomarker. In another aspect, the proinflammatory endophenotype is determined using TNFα, CRP, IL6, and IL10 biomarkers. In another aspect, the proinflammatory endophenotype proteins assayed are: TNFα, CRP, IL5, IL6, IL7, IL10 and IL18. In another aspect, a non-responder, or an adverse responder endophenotype indicates a decreased likelihood of pharmacological effectiveness of treatment by the NSAID in the patient. In another aspect, the expression level of the proinflammatory endophenotype is determined by detecting two or more proinflammatory endophenotype proteins. In another aspect, the expression level of the proinflammatory endophenotype is determined by detecting two or more proinflammatory endophenotype nucleic acids. In another aspect, the NSAID is selected from at least one of: naproxen, rofecoxib, ibuprofen, ketoprofen, tolmetin, diclofenac, fenoprofen, flurbiprofen, piroxicam, etodolac, ketorolac, imdomethacin, nabumetone, oxaprozin, or mefenamic acid. In another aspect, the method further comprises the step of ranking the expression of the proinflammatory endophenotype proteins and correlating them to an increased likelihood of pharmacological effectiveness of treatment with NSAID. In another aspect, the method further comprises the step of ranking the expression of the proinflammatory endophenotype proteins in the following order: CRP, TNFα, IL5, IL6, IL7, IL18 and IL10, and correlating them to the likelihood of pharmacological effectiveness of treatment by naproxen in the patient. In another aspect, the method further comprises the step of ranking the expression of the proinflammatory endophenotype proteins in the following order: IL10, CRP, IL6, IL18, IL7, TNFα, and IL5, and correlating them to the likelihood of pharmacological effectiveness of treatment by rofecoxib in the patient. In another aspect, the method has an accuracy of greater than 93, 94, 95, 96, 97, 98, 99, or 100% predictive value. In another aspect, the method further comprises the step of treating the patient with an NSAID if the patient has a responder endophenotype. In another aspect, the method further comprises the step of treating the patient with an NSAID if the patient has a stable endophenotype. In another aspect, the method further comprises the step of excluding patients from treatment with an NSAID if the patient has a non-responder or an adverse responder endophenotype. In another aspect, the method further comprises the step of stopping NSAID treatment for a patient that has a non-responder or an adverse responder endophenotype.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
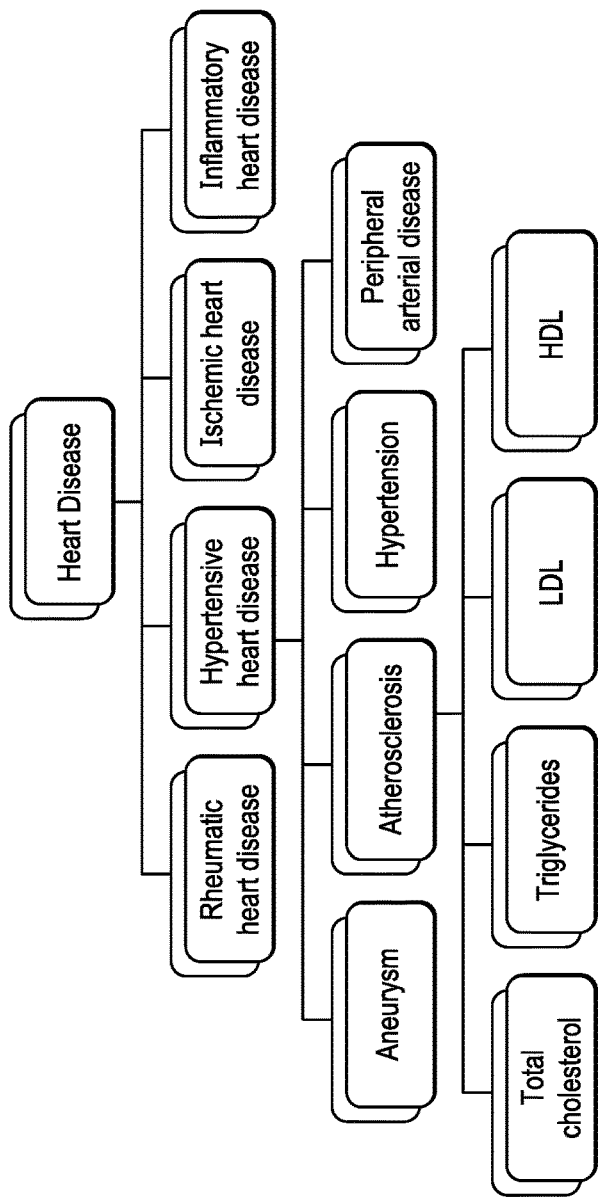
FIG. 1 is a diagram that shows a deconstruction of heart disease, specifically, atherosclerosis into generally disease conditions, and the markers used to identify atherosclerosis.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Despite billions of dollars expended, no new drugs for Alzheimer's disease (AD) have passed regulatory hurdles in over 10 years. In the inventor's prior work, they proposed that a paradigm shift is needed for the creation of a precision medicine model for AD, similar to that in cancer. Specifically, the present inventor has identified subgroups of patients suffering from AD based on biological dysfunctions. The ultimate goal was to provide a guided treatment regime (or a change in the same) using specific medications that address the specific biological dysfunction(s) suffered by a given patient suffering from AD.

More particularly, the present invention includes methods for the identification of specific sub-populations of patients suffering from AD. One subgroup is based on dysfunction of the inflammatory system (the proinflammatory endophenotype). In order to determine if the proinflammatory endophenotype can guide therapies, the inventor examined baseline (pre-randomization) blood samples from AD patients that participated in a therapeutic trial of NSAIDs in AD (rofecoxib, naproxen; the placebo arm was donepezil, an AChE inhibitor marketed as ARICEPT®). In this work, a drug-specific companion diagnostic was created that specifically, and robustly predicted treatment response to each therapy.

As used herein, the term "pro-inflammatory endophenotypes" refers to a response detectable at the nucleic acid or protein level that is indicative of an immune response that drives inflammation. When providing treatment for those subjects identified with the pro-inflammatory endophenotypes, the treatment can include the following. Nonsteroidal anti-inflammatory drugs (NSAIDs): Non-selective NSAIDs—non-selective NSAIDs would be selected for those patients falling into the high end of the proinflammatory endophenotype. As shown herein, non-selective NSAIDs (naproxen) were the superior treatment to selective NSAIDs (celecoxib). Non-selective NSAIDs can be tested with anyone falling within the high end of the proinflammatory endophenotype.

To determine a proinflammatory endophenotype, 2, 3, 4, 5, 6, 7, 8, 9, 10, 12, 13, 14, 15 or more of the following biomarkers in a sample selected for analysis. In one specific example, four biomarkers have been shown to be effective to determine the proinflammatory endophenotype, namely, TNFα, CRP, IL6, and IL10, to achieve a predictive value greater than 93, 94, 95, 96, 97, 98, 99, or 100%. Specifically, the biomarkers include: interleukin (IL)-7, tumor necrosis factor-alpha (TNFα), IL-5, IL-6, C-reactive protein (CRP), IL-10, tenascin C (TNC), intracellular adhesion molecule-1 (ICAM1), coagulation factor VII (FVII), 1309, tumor necrosis factor receptor-1 (TNFR1), alpha-2 macroglobulin (A2M), chemokine (C-C motif) ligand 17 (TARC), eotaxin3, vascular cell adhesion molecule-1 (VCAM1), thrombopoietin (TPO), fatty acid binding protein (FABP), IL-18, beta-2 microblogulin (B2M), serum amyloid A1 cluster (SAA), pancreatic polypeptide (PPY), Parkinson protein 7 (DJ1), beta amyloid (Aβ), tau, or α-synuclein, IL7, TNFα, IL5, IL6, CRP, IL10, TNC, ICAM1, FVII, 1309, TNFR1, A2M, TARC, eotaxin3, VCAM1, TPO, FABP, IL18, B2M, SAA, PPY, DJ1, Aβ, tau, or α-synuclein. Based on the results from the detection of these biomarkers at the nucleic acid or protein expression level, a high or a low proinflammatory endophenotype profile is determined from the level of expression of the two or more biomarkers. In one particular embodiment of the present invention, the proinflammatory endophenotypes markers are TNFα, CRP, IL6, and IL10, and in another example, the biomarkers are TNFα, CRP, IL5, IL6, IL7, IL10 and IL18.

As used herein, the terms "markers," "detectable markers" and "detectable labels" are used interchangeably to refer to compounds and/or elements that can be detected due to their specific functional properties and/or chemical characteristics, the use of which allows the agent to which they are attached to be detected, and/or further quantified if desired, such as, e.g., a nucleic acid, a protein, an antibody, an enzyme, radioisotope, electron dense particles, magnetic particles or chromophore that can be detected directly or indirectly, with or without amplification. There are many types of detectable labels, including fluorescent labels, which are easily handled, inexpensive and nontoxic.

Data source. Banked plasma samples from the Alzheimer's Disease Cooperative Studies (ADCS) anti-inflammatory clinical trial [23] were used. A full description of this trial, its endpoints and informed consent has been published elsewhere [23, 25], relevant portions incorporated herein by reference. This was a multicenter, randomized, double-blind, placebo-controlled parallel group trial with 1-year exposure to study medications across forty ambulatory treatment centers affiliated with the ADCS. Individuals with a diagnosis of probable AD (n=351) were recruited from December 1999 to November 2000 and randomized to one of the following treatment arms: rofecoxib (25 mg once daily), naproxen (220 mg twice-daily) or placebo. Inclusion criteria were as follows: age 50 or older, MMSE score of 13-26 and diagnosis of probable AD. Stable use of cholinesterase inhibitors was allowed. Exclusion criteria were as follows: presence of comorbid conditions that increased risk for adverse events associated with NSAID treatment (hypersensitivity to aspirin or NSAIDS, active peptic ulcer disease (5 year), renal insufficiency [serum creatinine level>1.5 mg/dL or >132.6 umol/L], clinically significant liver disease, poorly controlled hypertension, congestive heart failure, or bleeding ulcer); comorbid conditions that might respond to NSAIDs (e.g. inflammatory arthritis); history (2 month) of regular use of inflammatory medications (aspirin at a daily dose<=325 mg was allowed), neuroleptics, antidepressants, sedatives, anti-Parkinsonian medications, or any investigational treatment for AD. A total of 88 completed (111 randomized) the placebo arm, 90 completed (118 randomized) the naproxen arm and 89 completed (122 randomized) the rofecoxib arm. For the current study, proteomic and requisite clinical data were available for 156 participants who were included into the current analyses (naproxen n=51, placebo n=51, rofecoxib n=55).

Assays. All pre-randomization plasma samples were assayed in duplicate via a multi-plex biomarker assay platform via electrochemiluminescence using the SECTOR Imager 2400A from Meso Scale Discovery (MSD; www.mesoscale.com) per the inventors previously published protocols [8], relevant portions incorporated herein by reference. Blood samples were collected and processed per the original clinical trial methods [23] with samples stored centrally at the ADCS biorepository. The proteins assayed included TNFα, CRP, IL5, IL6, IL7, IL10 and IL18, which have been previously linked to the detection of AD [8, 10].

Statistical Analyses. Biomarker data were transformed using the Box-Cox transformation per previously published protocols [8, 10], relevant portions incorporated herein by reference. Support vector machine (SVM) analyses were utilized to build the proteomic profiles simultaneously classifying all outcome groups in R per the inventors previously published methods [8, 10-12, 26], relevant portions incorporated herein by reference. SVM analyses are capable of simultaneously taking into account large volume data to generate an overall profile (e.g., over and under-expression of select proteins) that most accurately classifies multiple outcomes rather than only binary outcomes. MMSE change scores were utilized as the outcome variables for the study (i.e. MMSE screening–MMSE 12-month follow-up=MMSE change). Participants were classified into four groups based on change in MMSE scores over 12-months: responders (improved MMSE scores of >=1 point over 12 mo), stable (no change in MMSE over 12 months), non-responders (MMSE decline of 1-2 points over 12 mo) or adverse responders (MMSE decline of 3 or more points over 12 mo). To build inflammatory profiles of treatment response, group status (i.e. treatment response) was utilized as the outcome variable in SVM models with pre-randomization inflammatory proteins as the predictor variable. In order to determine if the proinflammatory profile of treatment response was drug-specific, analyses were conducted utilizing the total sample as well as within specific study treatment arms.

Demographic characteristics of the cohort can be found in Table 1. The full characterization of the cohort can be found elsewhere [23, 25], relevant portions incorporated herein by reference. A total of 34 (22%) of participants showed an improved MMSE score over the course of the trail, 19 (12%) remained stable, 30 (19%) declined mildly (1-2 points) whereas 73 (47%) of the participants demonstrated a decline of 3 or more points on the MMSE over the 12-month period. First, an SVM-based proinflammatory profile was generated to predict treatment response amongst the entire cohort; results are in Table 2. The overall accuracy of the proinflammatory profile in predicting treatment response group membership was 93%. With regards to prediction of treatment response, the SVM generated proinflammatory profile was 88% (29 out of 34) accurate in detecting those participants that experienced improved cognitive function, 89% accurate in detecting those who remained stable, 100% (30 out of 30) accurate in detecting mild decline and 89% accurate in detecting those who declined 3 or more points on the MMSE over time (Table 2).

TABLE 1

Demographic Characteristics of the Sample Cohort

|  | Naproxen (n = 51) | Rofecoxib (n = 55) | Placebo (n = 51) |
| --- | --- | --- | --- |
| Age, mean (SD) | 74.0 (7.8) | 73.8 (7.3) | 73.8 (7.8) |
| Education, mean (SD) | 13.9 (3.2) | 13.9 (3.2) | 14.4 (3.2) |
| Gender (% female) | 48% | 54% | 55% |
| ApoE4 positive (%) | 71% | 69% | 68% |

Next, an SVM-based proinflammatory profile was generated separately for each treatment arm. Within the naproxen arm, a total of 10 (20%) of the participants demonstrated improvement in MMSE scores over 12-months, 4 (8%) remained stable, 10 (20%) demonstrated mild decline, whereas 26 (51%) declined 3 or more points. The naproxen-specific proinflammatory profile was 100% accurate in predicting all treatment response groups. For the rofecoxib arm, 9 (16%) participants demonstrated an improved MMSE score over time, 8 (15%) remained stable, 14 (25%) declined mildly, and 23 (42%) declined 3 or more points over 12-months. The rofecoxib-specific proinflammatory profile was 100% accurate in predicting all treatment response groups. Within the placebo group (i.e. cholinesterase inhibitors), 14 (27%) demonstrated improvement in MMSE scores, 6 (12%) remained stable, 11 (22%) declined mildly and 20 (39%) declined 3 or more points over 12-months (Table 2). The placebo-specific proinflammatory profile was 100% accurate in predicting all treatment response groups.

TABLE 2

Treatment Response Prediction Using Proteomic Profiling Analyses

|  | SVM Predicted Adverse Responder | SVM Predicted Non-Responder | SVM Predicted Stable | SVM Predicted Responder |
| --- | --- | --- | --- | --- |
| Total Sample (93% accurate) |  |  |  |  |
| Actual Adverse Responder | 65 | 2 | 2 | 4 |
| Actual Non-Responder | 0 | 30 | 0 | 0 |
| Actual Stable | 1 | 1 | 17 | 0 |
| Actual Responder | 3 | 2 | 0 | 29 |
| Naproxen Arm (100% accurate) |  |  |  |  |
| Actual Adverse Responder | 26 | 0 | 0 | 0 |
| Actual Non-Responder | 0 | 10 | 0 | 0 |
| Actual Stable | 0 | 0 | 4 | 0 |
| Actual Responder | 0 | 0 | 0 | 10 |
| Placebo Arm (100%) accurate |  |  |  |  |
| Actual Adverse Responder | 20 | 0 | 0 | 0 |
| Actual Non-Responder | 0 | 11 | 0 | 0 |
| Actual Stable | 0 | 0 | 6 | 0 |
| Actual Responder | 0 | 0 | 0 | 14 |
| Rofecoxib Arm (100% accurate) |  |  |  |  |
| Actual Adverse Responder | 23 | 0 | 0 | 0 |
| Actual Non-Responder | 0 | 14 | 0 | 0 |
| Actual Stable | 0 | 0 | 8 | 0 |
| Actual Responder | 0 | 0 | 0 | 9 |

Next, the importance plots of the proinflammatory profiles were examined across each study arm (see Table 3). As can be seen in Table 3, the relative importance of each marker within the drug-specific algorithm was different. For example, the three most important markers in predicting treatment response to naproxen were CRP, TNFα and IL5, respectively.

TABLE 3

Inflammatory Profile Variable Importance by Arm

| Marker Rank | Naproxen | Placebo | Rofecoxib |
| --- | --- | --- | --- |
| 1 | CRP | IL7 | IL10 |
| 2 | TNFα | IL18 | CRP |
| 3 | IL5 | CRP | IL6 |
| 4 | IL6 | IL6 | IL18 |
| 5 | IL7 | TNFα | IL7 |
| 6 | IL18 | IL10 | TNFα |
| 7 | IL10 | IL5 | IL5 |

Alternatively, the top three markers for the placebo (i.e., AChE inhibitor) group and rofecoxib group were IL7, IL18, CRP and IL10, CRP and IL6, respectively. Therefore, the proinflammatory profile that identified treatment response was, as hypothesized, drug-specific.

Lastly, the inventor applied the relative importance plot data for biomarker cut-scores to predict treatment outcomes within the naproxen arm. The top two markers within this arm were CRP and TNFα. Both CRP and TNFα were overexpressed as a function of treatment response (i.e. higher levels were associated with treatment response to naproxen). Therefore, tertile scores were created for both markers for creation of cut-scores per level of the proinflammatory endophenotype using only these two markers.

The cut-scores for inclusion into the naproxen proinflammatory endophenotype were as follows: low proinflammatory endophenotype=CRP<335.64 & TNFα<0.49 (10% of the arm); middle proinflammatory endophenotype=CRP of 335.64-1015.51 & TNFα of 0.49-0.63 (74% of the naproxen arm); high proinflammatory endophenotype=CRP>1015.52 & TNFα>0.64 (16% of the naproxen arm). When examining those specifically within the high end of the proinflammatory endophenotype, the naproxen group demonstrated significantly reduced decline in MMSE scores over a 12 mo period (F[1,6]=8.2, p=0.03; partial eta squared=0.58, observed power=0.7) as compared to the placebo group. Next, MMSE change scores were dichotomized into improvement versus stable or decline over the 12-mo period. The average score was 0.25 for the Placebo group (25% improved) and 0.63 for the Naproxen group (63% improved). The Naproxen group experienced significant improvement in MMSE scores over 12 months as compared to the Placebo group with age, gender, education and APOE4 genotype entered as covariates (F[1,6]=10.9, p=0.02, Partial Eta Square=0.65, observed power 0.79)(See Table 4). There was a trend towards those in the high end of the proinflammatory endophenotype who were treated with placebo (i.e., AChE inhibitor) to get significantly worse cognitively over time (p=0.07).

AD cases are at risk for more rapid progression as a result of taking NSAID drugs, that is, the NSAIDs are contraindicated.

This finding explains the failure to meet clinical endpoints for NSAIDs. The current findings, on the other hand, demonstrates that subgroups within AD patients exists and that baseline proinflammatory profiles predict treatment response for a select portion of patients.

The inventor further conducted analyses based on a novel four-biomarker profile. The biomarkers selected for this study were TNFα, CRP, IL6, and IL10. For these analyses, patients were classified as follows based on change in MMSE scores over time.

TABLE 5

Patient Classification.

| Patient Classification | Change in MMSE Scores |
|---|---|
| Responder | 0 or lower points decline on MMSE (stable or improved) |
| Non-Responder | 1-2 points decline on MMSE |
| Adverse Responder | 3 or more points decline on MMSE |

TABLE 4

Clinical Outcome Scores by Treatment Arm and Proinflammatory Endophenotype status

| Arm | MMSE Baseline | MMSE 12 mo | MMSE Change | CDR-SB Baseline | CDR-SB 12 mo | CDR-SB Change |
|---|---|---|---|---|---|---|
| Naproxen | | | | | | |
| Low (n = 7) | 17.1 (4.3) 14-26 | 16.1 (5.5) 7-24 | 1.5 (3.1) −2-7 | 7.9 (3.0) 2.5-12.0 | 9.8 (4.1) 3-15 | −2.5 (2.1) −5-0 |
| Middle (n = 36) | 20.7 (3.4) 13-26 | 16.5 (6.4) 4-25 | 4.2 (4.6) −2-19 | 6.1 (2.8) 1-12 | 8.4 (4.1) 2-18 | −2.6 (2.5) −8-2.5 |
| High (n = 8) | 21.1 (3.9) 14-15 | 21.2 (5.3) 15-28 | −0.13 (3.1) −3-5 p = 0.02* | 5.8 (2.7) 1-12 | 5.36 (3.0) 2-12 | 0.7 (2.5) −6.5-1 |
| Placebo | | | | | | |
| Low (n = 5) | 18.7 (3.6) 15-24 | 19.8 (4.4) 12-23 | −0.6 (3.5) −4-3 p = 0.07** | 5.7 (2.4) 3.5-10 | 7.0 (3.1) 3.5-11 | −1.2 (1.0) −2.5-0.0 |
| Middle (n = 42) | 21.5 (3.7) 13-27 | 19.9 (4.4) 12-23 | 2.0 (4.0) −4-12 | 5.3 (2.5) 1.5-13 | 6.8 (3.7) 1.5-16 | 1.9 (2.1) −7-1.5 |
| High (n = 4) | 20.7 (3.8) 15-25 | 16.3 (8.4) 5-24 | 4.8 (6.4) −2-12 | 6.1 (2.4) 2.5-9 | 7.8 (5.0) 3-13 | −2.0 (3.7) −5-2.5 |

NOTE:
sample size includes only those patients with all data available (baseline, 12 mo and change schores);
*significant difference as compared to placebo high proinflammatory group;
**as compared to the low end of the proinflammatory group in the naproxen arm.

These results demonstrate for the first time that NSAID therapy is associated with cognitive stability and benefit for a select subgroup of AD patients as well as adverse response among others.

Specifically, in the ADCS AD NSAID trial, 22% of participants demonstrated improved MMSE scores over time; however, 43% experienced a worsening of cognition of 3 or more points over time. In the follow-up analyses within the naproxen arm, the change in MMSE scores among the high proinflammatory AD receiving active therapy was significantly better than that observed in the placebo group. Therefore, treatment with NSAID medications is clinically appropriate for only a select subset of patients. These data also show that a significant portion of

TABLE 6

Treatment Response Prediction Using Four Biomarker Analyses Prediction by arm: Naproxen (68 patients) Prediction accuracy: 97.06%

| | Predicted Adverse Responder | Predicted Non-Responder | Predicted Responder |
|---|---|---|---|
| Actual Adverse Responder | 26 | 0 | 2 |
| Actual Non-Responder | 0 | 10 | 0 |
| Actual Responder | 0 | 0 | 30 |

TABLE 7

Treatment Response Prediction Using Four Biomarker Analyses Prediction by arm: Rofecoxib (55 patients) Prediction accuracy: 98.18%

|  | Predicted Adverse Responder | Predicted Non-Responder | Predicted Responder |
|---|---|---|---|
| Actual Adverse Responder | 23 | 0 | 1 |
| Actual Non-Responder | 0 | 14 | 0 |
| Actual Responder | 0 | 0 | 17 |

TABLE 8

Treatment Response Prediction Using Four Biomarker Analyses Prediction by arm: Naproxen and Rofecoxib (Combined) (123 patients) Prediction accuracy: 88.62%

|  | Predicted Adverse Responder | Predicted Non-Responder | Predicted Responder |
|---|---|---|---|
| Actual Adverse Responder | 41 | 1 | 4 |
| Actual Non-Responder | 1 | 22 | 0 |
| Actual Responder | 7 | 1 | 46 |

TABLE 9

Inflammatory Profile Variable Importance by Arm (Based on Four Biomarker Analyses)

| Biomarker Rank | Naproxen | Rofecoxib | Naproxen and Rofecoxib (Combined) |
|---|---|---|---|
| 1 | CRP | IL6 | CRP |
| 2 | IL6 | CRP | IL6 |
| 3 | TNFα | IL10 | IL10 |
| 4 | IL10 | TNFα | TNFα |

When examining treatment response within arms, the proinflammatory profiles (1) changed significantly based on drug administered and (2) became more accurate. The variable importance plots explain the significantly improved performance. Specifically, the overall algorithm did not take into account drug-specific effects (but is able to) and the variable importance plots clearly indicate a different pattern per arm. Using only two of the biomarkers from the naproxen-specific algorithm (CRP and TNFα), cut-scores were generated to create subgroups that predict treatment response. Those in the high end of the proinflammatory endophenotype experience significant improvement while there was a trend towards those in the low end to experience significant decline. This two-marker approach provides a more simplistic method for demonstrating the proof-of-concept; however, the multi-marker SVM approach is more accurate and is preferable for generating profiles that may be utilized for enriching into clinical trials.

When taken within the context of previously conducted clinical trials, the present invention can also be used to evaluate data from these trials and select for subgroups of AD patients for which the treatment was successful. The assays from pre-randomization biobanked samples from other trials can be used for validation purposes and the patients sub-divided into the subgroups of the present invention. The proinflammatory biomarker profile can also be utilized for patient selection and stratification for novel clinical trials utilizing NSAID therapy to treat and perhaps prevent AD with the current methods utilized for targeted patient enrichment. That is, only those patients with baseline alterations of the proinflammatory profile would be enrolled into the study. The enrichment of such a targeted population would significantly reduce the overall cost of the trial by: (1) reducing the required number of patients to detect the predicted response, as well as, (2) reduce the time to market as the effect size would be much larger and be detectable in briefer trials. Additionally, the removal of those patients most likely to experience harm from the drug is of tremendous benefit.

Profiling biological pathways, including inflammation, highlights novel pathways relevant to AD. Additionally, biomarkers of inflammation have consistently been important in a blood-based algorithm of disease presence [10-13]. Histopathologically, inflammatory markers have been found in association with both neurofibrillary tangles [27] and senile plaques [28] in AD tissue. Longitudinally, studies also support the link between inflammation and AD. For example, Schmidt and colleagues [14] analyzed data from the Honolulu-Aging Study & Honolulu-heart study and found that increased CRP levels at midlife were associated with increased risk for the development of AD, as well as VaD 25-years later.

There is a large base of epidemiological evidence supporting the notion that anti-inflammatory compounds reduce the risk of developing AD. In a prospective, population-based cohort study of nearly 7,000 individuals 55 years of age and older, all of whom were dementia-free at baseline, long-term use of NSAIDs was associated with a reduced risk of developing AD (relative risk=0.20, CI=0.05-0.83)[15]. When analyzing data from the Cache County Study, Anthony and colleagues [16] found that use of non-aspirin NSAIDs alone reduced the risk of developing AD (Odds Ratio [OR]=0.43, CI=0.23-0.75) and that use of non-aspirin NSAIDs and aspirin reduced that risk even further (OR=0.17, CI=0.04-0.48). A meta-analysis of nine published studies (pooled sample size=14,654) further supported the notion of a protective effect of NSAID use in terms of AD development with the relative risk of 0.27 (95% CI=0.13-0.58) associated with long-term use [17].

Based on these findings, anti-inflammatory compounds have the potential for treating those suffering from AD and other neurodegenerative diseases [13, 16-21], and three clinical trial have been completed, one on AD[18], one on MCI[22], and the Alzheimer's Disease Anti-inflammatory Prevention Trial (ADAPT)[24, 29]. These studies, based on the available literature, utilized a traditional NSAID (naproxen) as well as a COX-2 inhibitor. Naproxen was utilized based on a several reasons. First, several epidemiological studies (see above) suggest a protective effect of non-selective NSAIDs against neurodegeneration[30].

NSAIDs block microglial activation in vitro [31, 32] and appear to reduce accumulation of activated microglia in the AD brain[33]. On the other hand, non-selective NSAIDS are also associated with toxicity and high drop-out rates [34], which makes them difficult for studies of AD patients. Rofecoxib, a COX-2 inhibitor was utilized for several reasons. First, COX-2 may play a central role in neurodegeneration via excitotoxicity (glutamate and kainic acid) pathways[35]. Thus, the present invention for the first time provides for a detailed analysis and determination of those AD patients that will respond positively to NSAID treatment.

COX-2 expression (mRNA and protein) has also been found upregulated in human AD brains[36]. At the time, it was also thought that COX-2 inhibitors would be less toxic than non-selective NSAIDs. Despite the significant basic, clinical and epidemiological literature in support of the use of NSAIDs in AD, none of those trials successfully met targeted clinical outcomes. Therefore, the effect of NSAIDs on AD was previously mixed.

The present invention addresses what none of those trials found (and a possible reason why they failed); specific subsets of patients where inflammation played a prominent role in cognitive loss and whom were most likely to benefit from the trial. The current results demonstrate that targeted treatment with NSAID medications may benefit select subsets of patients with AD, while being contra-indicated for others. Additionally, given that the placebo group was treated with cholinesterase inhibitors, the current approach shows the generation of a proteomic profile of treatment response to such medication.

The current findings are as follows: (1) the use of NSAIDs (e.g., naproxen) to effectively treat certain individuals with AD and, more importantly, (2) provide a novel method for clinical trials in AD. Specifically, the present invention demonstrates that subgroups of AD patients exist, within the heterogeneous categorization of AD, and that these subgroups are useful in determining which patients will respond best to particular medications. It also serves to demonstrate which patients will not respond, or may respond adversely, to particular medications.

These results are a paradigm shift in the conceptualization of the therapeutic approach to AD. By way of explanation, and in no way a limitation of the present invention, the inventor proposes a model that targets select patients to specific interventions based on the subgroup(s) to which patient belongs. As an analogy, the approach herein is adopted from that utilized in the successful treatment of cardiovascular disease. For example, FIG. 1 outlines the therapeutic approach to atherosclerotic heart disease, which is only one form of heart disease. In cardiology, one does not treat "atherosclerosis" as a diagnostic category, but rather, specific types of atherosclerotic factors are treated. However, in the prevailing models for the treatment of AD, all patients are enrolled into clinical trials based on a general clinical diagnosis.

Figure 2:
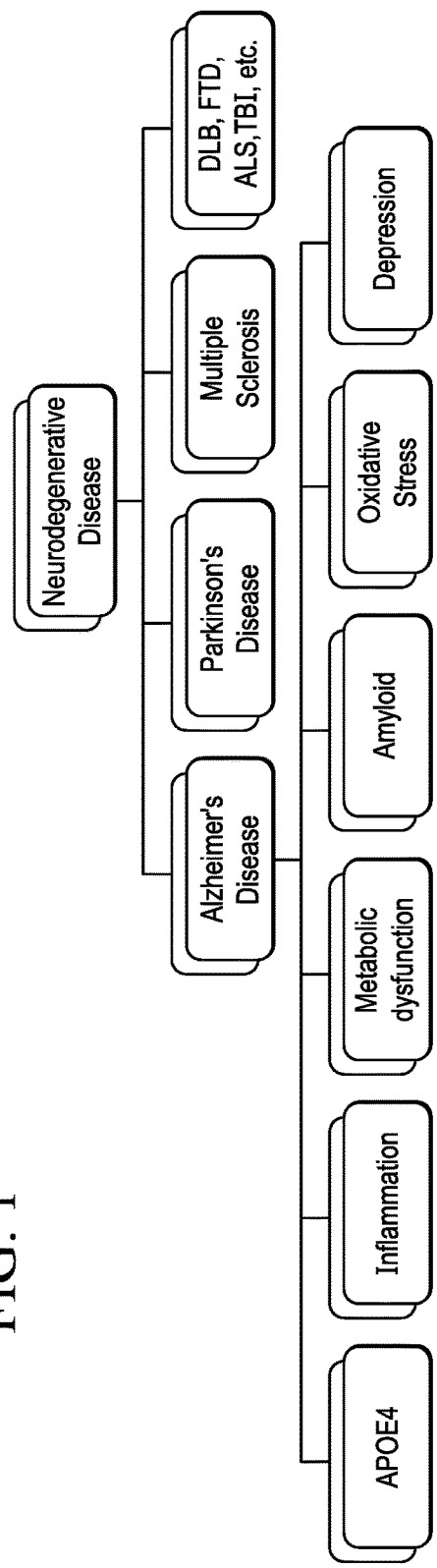
FIG. 2 is a diagram that shows a model for deconstructing Alzheimer's Disease into subgroups based on the findings of the present invention.

In FIG. 2, the inventor proposes a first-step towards a more refined model for treating AD. In the inventor's prior work several subgroups of AD patients were identified based on proteomic and neuropsychiatric data. When combined with other findings, the specific subgroups proposed currently in the model include: inflammation [10, 12, 13], APOE4 genotype[37], metabolic dysfunction[38], amyloid, oxidative stress[39], and depression[40, 41]. The current findings validate a person-centered AD therapeutic model via the inflammatory subgroup. Additionally, as with CVD, the presence of dysfunction in one sub-category does not preclude the presence of abnormality in another, and the current model directly provides a conceptual framework for combination therapy. Taken together, these findings show a novel approach to treating specific subsets of AD patients. For example, the present invention can be used to assay existing biorepositories of >20,000 samples across previously conducted clinical trials, which can be the first step towards the generation of a person-centered therapeutic approach to the treatment and prevention of AD and other neurodegenerative diseases.

As such, the present invention provides: (1) a companion diagnostic to identify specific populations of patients most likely to respond to therapy; (2) a companion diagnostic to identify specific patients most likely to suffer from adverse events (and should not be prescribed treatment); (3) novel technology that can be used to revolutionize clinical trials in AD to only enroll those patients that have a high likelihood of responding to therapy, thereby reducing the sample size (and cost) of trials significantly; (4) technology that has a tremendous impact on clinical trials by reducing the timeframe needed to complete trials by only enrolling those most likely benefit (both #3 and #4 have significant impacts on cost containment); and/or (5) a companion diagnostic that can be used to identify patients that are likely to remain stable or improve from therapy rather than only declining more slowly (i.e. the therapeutic impact of the intervention is much larger).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s)

or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] Association As. 2013 Alzheimer's Disease facts and figures. Alzheimers Dement. 2013; 9:1-72.
[2] Hurd M D, Martorell P, Delavande A, Mullen K J, Langa K M. Monetary costs of dementia in the United States. N Engl J Med. 2013; 368:1326-1334.
[3] Lyketsos C G, Szekely C A, Mielke M M, Rosenberg P B, Zandi P P. Developing new treatments for Alzheimer's disease: The who, what, when, and how of biomarker-guided therapies. Int Psychogeriatr. 2008; 20:871-889.
[4] Henchcliffe C, Dodel R, Beal M F. Biomarkers of Parkinson's disease and Dementia with Lewy bodies. Prog Neurobiol. 2011; 95:601-613.
[5] Hu W T, Chen-Plotkin A, Arnold S E, Grossman M, Clark C M, Shaw L M, McCluskey L, Elman L, Karlawish J, Hurtig H I, Siderowf A, Lee V M, Soares H, Trojanowski J Q. Biomarker discovery for Alzheimer's disease, frontotemporal lobar degeneration, and Parkinson's disease. Acta Neuropathol. 2010; 120:385-399.
[6] Durrenberger P F, Fernando F S, Kashefi S N, Bonnert T P, Seilhean D, Nait-Oumesmar B, Schmitt A, Gebicke-Haerter P J, Falkai P, Grunblatt E, Palkovits M, Arzberger T, Kretzswchmar H, Dexter D T, Reynolds R. Common mechanisms in neurodegeneration and neuroinflammation: a BrainNet Europe gene expression microarray study. J Neural Transm. 2014.
[7] Heneka M T, Kummer M P, Latz E. Innate immune activation in neurodegenerative disease. Nat Rev Immunol. 2014; 14:463-477.
[8] O'Bryant S E, Xiao G, Zhang F, Edwards M, German D, Yin X, Como T, Reisch J, Huebinger H M, Graff-Radford N, Dickson D, Barber R C, Hall J, O'Suilleabhain P, Grammas P. Validation of a serum screen for Alzheimer's disease across assay platforms, species and tissues. J Alzheimers Dis. 2014; 42:1325-35.
[9] O'Bryant S E, Johnson L, Edwards M, Soares H, Devous M D, Ross S, Rohlfing G, Hall J; Texas Research and Care Consortium. The link between c-reactive protein and Alzheimer's disease among Mexican Americans. J Alzheimers Dis. 2013; 34:701-706.
[10] O'Bryant S E, Xiao G, Barber R, Reisch J, Doody R, Fairchild T, Adams P, Waring S, Diaz-Arrastia R; Texas Alzheimer's Research Consortium. A serum protein-based algorithm for the detection of Alzheimer disease. Arch Neurol. 2010; 67:1077-1081.
[11] O'Bryant S E, Xiao G, Barber R, Huebinger R, Wilhelmsen K, Edwards M, Graff-Radford N, Doody R, Di. A blood-based screening tool for Alzheimer's disease that spans serum and plasma: Findings from TARC and ADNI. PLoS ONE. 2011; 6:e28092.
[12] O'Bryant S, Xiao G, Barber R, Reisch J, Hall J, Cullum C M, Doody R, Fairchild T, Adams P, Wilhelmsen K, Diaz-Arrastia R. A blood based algorithm for the detection of Alzheimer's disease. Dement Geriatr Cogn Disord. 2011; 32:55-62.
[13] O'Bryant S E, Waring S C, Hobson V, Hall J R, Moore C B, Bottiglieri T, Massman P, Diaz-Arrastia R. Decreased C-reactive protein levels in alzheimer disease. J Geriatr Psychiatry Neurol. 2010; 23:49-53.
[14] Schmidt R, Schmidt H, Curb J D, Masaki K, White L R, Launer L J. Early inflammation and dementia: a 25-year follow-up of the Honolulu-Asia Aging Study. Ann Neurol. 2002; 52:168-174.
[15] In't Veld B A, Ruitenberg, A, Hofman, A, Launer, U, van Duijn, C M, Stijnen, T, Breteler M M, Stricker B H. Nonsteroidal antiinflammatory drugs and the risk of Alzheimer's disease. N Engl J Med. 2001; 345:1515-1521.
[16] Anthony J C, Brenner J C, Zandi P P, Meyer M R, Jurasova I, Norton M C, Stone S V. Reduced prevalence of A D in users of NSAIDs and H2 receptor antagonists: the Cache County study. Neurology. 2000; 54:2066-2071.
[17] Etminan M, Gill S, Samii A. Effect of non-steroidal anti-inflammatory drugs on risk of Alzheimer's disease: Systematic review and meta-analysis of observational studies. BMJ. 2003; 327:128.
[18] Aisen P S, Schafer K A, Grundman M, Pfeiffer E, Sano M, Davis K L, Farlow M R, Jin S, Thomas R G, Thal I I, Alzheimer's Disease Cooperative Study. Effects of rofecoxib or naproxen vs placebo on Alzheimer disease progression: a randomized controlled trial. JAMA. 2003; 289:2819-2826.

[19] Gasparini L, Ongini E, Wenk G. Non-steroidal anti-inflammatory drugs (NSAIDs) in Alzheimer's disease: Old and new mechanisms of action. J Neurochem. 2004; 91:521-536.

[20] Hirohata M, Ono K, Naiki H, Yamada M. Non-steroidal anti-inflammatory drugs have anti-amyloidogenic effects for Alzheimer's B-amyloid fibrils in vitro. Neuropharmacology. 2005; 49:1088-1099.

[21] Klegeris A, McGeer P L. Non-steroidal anti-inflammatory drugs (NSAIDs) and other anti-inflammatory agents in the treatment of neurodegenerative disease. Curr Alzheimer Res. 2005; 2:355-365.

[22] Thal I I, Ferris S H, Kirby L, Block G A, Lines C R, Yuen E, Assaid C, Nessly M L, Norman B A, Baranak C C, Reines S A; Rofecoxib Protocol 078 study group. A randomized, double-blind, study of rofecoxib in patients with mild cognitive impairment. Neuropsychopharmacology. 2005; 30:1204-1215.

[23] Aisen P S, Schafer K A, Grundman M, Knopman D, Tabet N. Neither rofecoxib nor naproxen slows cognitive decline in people with mild-to-moderate Alzheimer's disease. Evidence-Based Healthcare. 2003; 7:200-201.

[24] ADAPT Research Group, Lyketsos C G, Breitner J C, Green R C, Martin B K, Meinert C, Piantadosi S, Sabbagh M. Naproxen and celecoxib do not prevent A D in early results from a randomized controlled trial. Neurology. 2007; 68:1800-1808.

[25] Grundman M, Thal J L. Treatment of Alzheimer's disease: rationale and strategies. Neurologic Clinics. 2000; 18:807-827.

[26] O'Bryant S E, Xiao G, Edwards M, Devous M, Gupta V B, Martins R, Zhang F, Barber R; Texas Alzheimer's Research and Care Consortium (TARCC). Biomarkers of Alzheimer's disease among Mexican Americans. J Alzheimers Dis. 2013; 34:841-849.

[27] Duong T, Nikolaeva M, Acton P J. C-reactive protein-like immunoreactivity in the neurofibrillary tangles of Alzheimer's disease. Brain Res. 1997; 749:152-156.

[28] Iwamoto N, Nishiyama E, Ohwada J, Arai H. Demonstration of CRP immunoreactivity in brains of Alzheimer's disease: immunohistochemical study using formic acid pretreatment of tissue sections. Neurosci Lett. 1994; 177:23-26.

[29] Breitner J C, Baker L D, Montine T J, Meinert C L, Lyketsos C G, Ashe K H, Brandt J, Craft S, Evans D E, Green R C, Ismail M S, Martin B K, Mullan M J, Sabbagh M, Tariot P N, ADAPT Research Group. Extended results of the Alzheimer's disease anti-inflammatory prevention trial. Alzheimers Dement. 2011; 7:402-411.

[30] McGeer E G, McGeer P L. The importance of inflammatory mechanisms in Alzheimer disease. Exp Gerontol. 1998; 33:371-378.

[31] Gottschall P E. Beta-amyloid induction of gelatinase B secretion in cultured microglia: inhibition by dexamethasone and indomethacin. Neuroreport. 1996; 7:3077-3080.

[32] Netland E E, Newton J L, Majocha R E, Tate B A. Indomethacin reverses the microglial response to amyloid beta. Neurobiol Aging. 1998; 19:201-204.

[33] Mackenzie I R, Munoz D G. Nonsteroidal anti-inflammatory drugs use and Alzheimer-type pathology in aging. Neurology. 1998; 50:986-990.

[34] Rogers J, Kirby L C, Hempelman S R, Berry D L, McGeer P L, Kaszniak A W, Zalinski J, Cofield M, Mansukhani L, Willson P et al. Clinical trial of indomethacin in Alzheimer's disease. Neurology. 1993; 43:1609-1611.

[35] Tocco G, Freire-Moar J, Schreiber S S, Sakhi S H, Aisen P S, Pasinetti G M. Maturational regulation and regional induction of cyclooxygenase-2 in rat brain: implications for Alzheimer's disease. Exp Neurol. 1997; 144:339-349.

[36] Pasinetti G M, Aisen P S. Clycooxygenase-2 expression is increased in frontal cortex of Alzheimer's disease brain. Neuroscience. 1998; 87:319-324.

[37] Hall J R, Wiechmann A R, Johnson L A, Edwards M, Barber R C, Cunningham R, Singh M, O'Bryant S E. The impact of APOE status on relationship of biomarkers of vascular risk and systemic inflammation to neuropsychiatric symptoms in Alzheimer's disease. J Alzheimers Dis. 2014; 40:887-896.

[38] O'Bryant S E, Johnson L, Reisch J, Edwards M, Hall J, Barber R, Devous D M Sr, Royall D, Singh M. Risk factors for mild cognitive impairment among Mexican Americans. Alzheimers Dement. 2013; 9:622-631.

[39] Cunningham R L, Singh M, O'Bryant S E, Hall J R, Barber R C. Oxidative stress, testosterone, and cognition among caucasian and mexican-american men with and without Alzheimer's disease. J Alzheimers Dis. 2014; 40:563-573.

[40] Johnson L A, Hall J R, O'Bryant S E. A Depressive Endophenotype of Mild Cognitive Impairment and Alzheimer's Disease. PLoS ONE. 2013; 8:e68848.

[41] Johnson L A, Sohrabi H R, Hall J R, Taddei K, Edwards M, O'Bryant S E, Martins R N. A depressive endophenotype of poorer cognition among cognitively healthy community-dwelling adults: Results from the Western Australia Memory Study. Int J Geriatr Psychiatry. 2015 August; 30(8):881-6.

What is claimed is:

1. A method for identifying a patient response to treatment for Alzheimer's Disease with a non-steroidal anti-inflammatory drug (NSAID) comprising:
obtaining a blood, plasma, or serum sample from the patient;
determining a presence of a proinflammatory endophenotype associated with Alzheimer's disease in the blood, plasma, or serum sample of the patient;
using the proinflammatory endophenotype to detect a treatment response from the patient, wherein the method has an accuracy of greater than 93, 94, 95, 96, 97, 98, 99, or 100% predictive value; and
administering the NSAID to a responder or a stable treatment response phenotype group patient.

2. The method of claim 1, wherein the proinflammatory endophenotype is determined from a CRP and a TNFα biomarker; or TNFα, CRP, IL6, and IL10; or TNFα, CRP, IL5, IL6, IL7, IL10 and IL18.

3. The method of claim 1, wherein the treatment response is selected from a responder, a stable responder, a non-responder, or an adverse responder; or the treatment is contraindicated if the patient is in a non-responder, or an adverse responder group.

4. The method of claim 1, wherein the expression level of the proinflammatory endophenotype is determined by detecting the proteins, nucleic acids, or both.

5. The method of claim 1, wherein the NSAIDs are selected from at least one of: naproxen, rofecoxib, ibuprofen, ketoprofen, tolmetin, diclofenac, fenoprofen, flurbiprofen, piroxicam, etodolac, ketorolac, imdomethacin, nabumetone, oxaprozin, or mefenamic acid.

6. The method of claim 1, further comprising the step of ranking the expressions of the proinflammatory endophenotype proteins and correlating them to the NSAID; ranking the expressions of the proinflammatory endophenotype proteins in the following order: CRP, TNFα, IL5, IL6, IL7, IL18 and IL10, and correlating them to a response to naproxen; or ranking IL10, CRP, IL6, IL18, IL7, TNFα, and IL5, and correlating them to a response to rofecoxib.

7. The method of claim 1, further comprising the step of excluding patients from treatment with NSAIDs if the patients have a non-responder or an adverse responder treatment response phenotype or stopping NSAID treatment for patients in which NSAIDs are contraindicated.

8. A method for identifying a patient response to treatment for Alzheimer's Disease with a non-steroidal anti-inflammatory drug (NSAID) comprising:
   obtaining a blood, plasma, or serum sample from the patient;
   determining a presence of a proinflammatory endophenotype associated with Alzheimer's disease in the blood, plasma, or serum sample of the patient;
   using the proinflammatory endophenotype to detect a treatment response from the patient;
   determining a treatment type for the detected treatment response from the patient, the determining of the treatment type including:
      ranking the expressions of the proinflammatory endophenotype proteins and correlating them to the NSAID;
      ranking the expressions of the proinflammatory endophenotype proteins in the following order: CRP, TNFα, IL5, IL6, IL7, IL18 and IL10, and correlating them to a response to naproxen; or
      ranking IL10, CRP, IL6, IL18, IL7, TNFα, and IL5, and correlating them to a response to rofecoxib; and
   administering the NSAID, naproxen, or rofecoxib to a responder or a stable treatment response phenotype group patient based upon the determined treatment type.

* * * * *

UNITED STATES PATENT AND TRADEMARK OFFICE
CERTIFICATE OF CORRECTION

Page 1 of 1

PATENT NO. : 12,287,324 B2
APPLICATION NO. : 16/962917
DATED : April 29, 2025
INVENTOR(S) : O'Bryant It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1043 days.

Signed and Sealed this
Sixteenth Day of December, 2025

John A. Squires
*Director of the United States Patent and Trademark Office*